United States Patent
Yoshida et al.

(10) Patent No.: US 6,254,973 B1
(45) Date of Patent: *Jul. 3, 2001

(54) FLUORINE-CONTAINING POLYFUNCTIONAL (METH) ACRYLATE, FLUORINE CONTAINING MONOMER COMPOSITION, LOW REFRACTIVITY MATERIAL, AND REFLECTION REDUCING FILM

(75) Inventors: Tatsurou Yoshida; Yasuhiro Kimura, both of Tsukuba; Kenji Watanabe, Makabemachi; Tomoyuki Ikeda; Tetsuya Itoh, both of Tsukuba; Yoshitaka Goto, Yawaramura, all of (JP)

(73) Assignee: NOF Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/945,228

(22) PCT Filed: Feb. 12, 1997

(86) PCT No.: PCT/JP97/00356

§ 371 Date: Oct. 10, 1997

§ 102(e) Date: Oct. 10, 1997

(87) PCT Pub. No.: WO97/30021

PCT Pub. Date: Aug. 21, 1997

(30) Foreign Application Priority Data

| Feb. 14, 1996 | (JP) | 8-026473 |
| Feb. 21, 1996 | (JP) | 8-033808 |
| Mar. 14, 1996 | (JP) | 8-057264 |
| Aug. 19, 1996 | (JP) | 8-217449 |
| Nov. 8, 1996 | (JP) | 8-296506 |

(51) Int. Cl.⁷ .......................... B32B 27/30; C08F 136/22; C08F 236/16; C08F 236/22

(52) U.S. Cl. .......................... 428/212; 428/421; 526/242; 526/245; 560/264

(58) Field of Search .................................... 428/421, 212; 526/242, 245; 560/264

(56) References Cited

U.S. PATENT DOCUMENTS

| 4,456,647 | * | 6/1984 | Schönfelder et al. | 428/216 |
| 4,503,186 | * | 3/1985 | Sugio et al. | 525/63 |
| 5,275,864 | * | 1/1994 | Kenmochi | 428/156 |

FOREIGN PATENT DOCUMENTS

| 62-22735 | 1/1987 | (JP). |
| 62-199643 | 9/1987 | (JP). |
| 3-215453 | 9/1991 | (JP). |
| 4-356443 | 12/1992 | (JP). |

\* cited by examiner

Primary Examiner—Paul Thibodeau
Assistant Examiner—Ramsey Zacharia
(74) Attorney, Agent, or Firm—Darby & Darby

(57) ABSTRACT

Fluorine-containing polyfunctional (meth)acrylate represented by the formula (1), a monomer composition containing the (meth)acrylate, a low refractivity material prepared by curing the monomer composition, and a reflection reducing film provided with the low refractivity material.

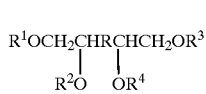

(1)

wherein $R^1$, $R^2$, $R^3$, and $R^4$ are the same or different groups, and each stands for a hydrogen atom, an acryloyl group, or a methacryloyl group, at least one of $R^1$ and $R^2$ and at least one of $R^3$ and $R^4$ stand for an acryloyl group or a methacryloyl group, R stands for a fluoroalkylene group having 2 to 12 carbon atoms and 2 or more fluorine atoms.

12 Claims, 12 Drawing Sheets

FLUORINE-CONTAINING POLYFUNCTIONAL (METH) ACRYLATE, FLUORINE CONTAINING MONOMER COMPOSITION, LOW REFRACTIVITY MATERIAL, AND REFLECTION REDUCING FILM

BACKGROUND ART

The present invention relates to novel fluorine-containing polyfunctional (meth)acrylate; monomer compositions which can be used as a starting material for preparing a low refractivity material which has both high surface hardness and low refractive index and which can be applied to the surface of various kinds of substrates; a low refractivity material prepared by curing the monomer composition by polymerization; and a reflection reducing film provided with the low refractivity material.

Compounds having a fluorine atom have low refractive index, and can be used for antireflection films or a clad material for optical fibers. In either applications, the lower the refractive index of the compound, the better the property of the products. There are proposed, for example, application of fluorine-containing (meth)acrylate polymers, copolymers of fluorine-containing (meth)acrylate with other monomers, tetrafluoroethylene polymers, copolymers of vinylidene fluoride and tetrafluoroethylene, or copolymers of vinylidene fluoride and hexafluoropropylene to optical fibers (Japanese Laid-open Patent Application Nos. 59-84203, 59-84204, 59-98116, 59-147011, and 59-204002).

Recently, there has attempted to apply solvent-soluble fluorine-containing polymers having low refractive index such as fluoroalkyl acrylate polymers, fluoroalkyl methacrylate polymers, or amorphous perfluoro resins such as CYTOP (trade name) manufactured by ASAHI GLASS COMPANY, or TEFRON AF (trade name) manufactured by E.I. du Pont de Nemours and Co. to reflection reducing films (Japanese Laid-open Patent Application Nos. 64-16873, 1-149808, and 6-115023).

These fluorine-containing resins, however, are non-crosslinked resins, and thus have low surface hardness after curing, inferior abrasion resistance, and insufficient adhesion.

For the purpose of improving the surface hardness, there has been proposed cross-linked polymers prepared from a suitable mixture of fluorine-containing monofunctional (meth)acrylate or fluorine-containing bifunctional (meth)acrylate and polyfunctional (meth)acrylate not containing fluorine (Japanese Laid-open Patent Application Nos. 58-105943, 62-199643, and 62-250047). The refractive index and the surface hardness of these cross-linked polymers may be adjusted to some extent by suitably selecting the content of fluorine in the fluorine-containing (meth)acrylate, or the mixing ratio of the fluorine-containing (meth)acrylate to the polyfunctional (meth)acrylate not containing fluorine. However, the fluorine-containing monofunctional (meth)acrylate and the polyfunctional (meth)acrylate are not compatible, and do not dissolve mutually at an arbitrary ratio. Therefore, sufficiently low refractive index cannot be achieved. On the contrary, the fluorine-containing bifunctional (meth)acrylate and the polyfunctional (meth)acrylate mutually dissolve at an arbitrary ratio. However, if the content of fluorine atoms in the cross-linked polymer is increased for reducing the refractive index, the cross-linking density is lowered. Accordingly, it is impossible to suffice both the low refractive index and the high surface hardness, and it is difficult to give sufficient surface hardness to the optical fibers and the reflection reducing film. Further, sufficient adhesion cannot be achieved.

There is also proposed fluorine-containing hydroxy (meth)acrylate for the purpose of improving the adhesion and for use as a starting material for other fluorine-containing (meth)acrylates (Japanese Laid-open Patent Application Nos. 4-321660, 4-356443, and 4-356444). However, since these compounds are monofunctional (meth)acrylate, the surface hardness after curing is low, and the abrasion resistance is inferior.

DISCLOSURE OF THE INVENTION

It is an object of the present invention to provide fluorine-containing polyfunctional (meth)acrylate which gives fluorine compounds having sufficiently low refractive index, sufficiently high surface hardness, and adhesion.

It is another object of the present invention to provide a low refractivity material having low refractive index and superior surface hardness, a reflection reducing film, and fluorine-containing monomer compositions which can be used as a starting material for such material and film.

According to the present invention, there is provided fluorine-containing polyfunctional (meth)acrylate represented by the formula (1):

wherein $R^1$, $R^2$, $R^3$, and $R^4$ are the same or different groups and each stands for a hydrogen atom, an acryloyl group, or a methacryloyl group, at least one of $R^1$ and $R^2$ and at least one of $R^3$ and $R^4$ stand for an acryloyl group or a methacryloyl group, R stands for a fluoroalkylene group having 2 to 12 carbon atoms and two or more fluorine atoms.

According to the present invention, there is provided a fluorine-containing monomer composition comprising 5 to 100% by weight of said fluorine-containing polyfunctional (meth)acrylate represented by the formula (1) above.

According to the present invention, there is further provided a low refractivity material having refractive index of 1.49 or lower prepared by a method comprising the step of curing the monomer composition by polymerization.

According to the present invention, there is provided a reflection reducing film comprising a transparent substrate, a layer of the low refractivity material above, and optionally at least one material layer between the transparent substrate and the layer of the low refractivity material.

PREFERRED EMBODIMENTS OF THE PRESENT INVENTION

Figure 1:
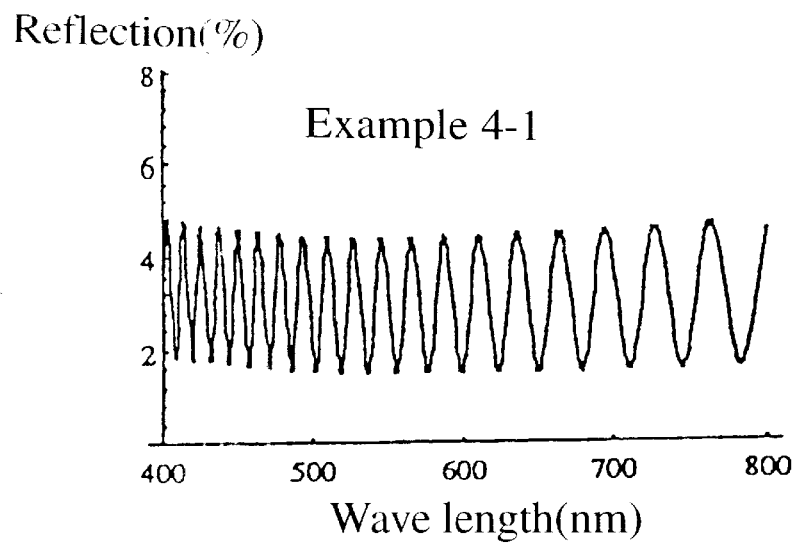
FIG. 1 is a graph showing the results of the measurements of the spectral reflectance in Example 4-1.

The fluorine-containing polyfunctional (meth)acrylate of the present invention is represented by the formula (1) above. Specifically, the present fluorine-containing polyfunctional (meth)acrylate may be fluorine-containing bifunctional (meth)acrylate having a (meth)acryloyl group and a hydroxyl group wherein one of $R^1$ and $R^2$ stands for an acryloyl group or a methacryloyl group, the other of $R^1$ and $R^2$ stands for a hydrogen atom, one of $R^3$ and $R^4$ stands for an acryloyl group or a methacryloyl group, and the other of $R^3$ and $R^4$ stands for a hydrogen atom (referred to as diester A hereinbelow), fluorine-containing trifunctional (meth)acrylate having a (meth)acryloyl group and a hydroxyl group wherein one of $R^1$, $R^2$, $R^3$, and $R^4$ stands for a hydrogen atom and each of the remaining three of $R^1$, $R^2$, $R^3$, and $R^4$ stands for an acryloyl group or a methacryloyl group (referred to as triester A hereinbelow), or fluorine-containing tetrafunctional (meth)acrylate wherein $R^1$, $R^2$, $R^3$, and $R^4$ are the same or different groups, and each stands for an acryloyl group or a methacryloyl group (referred to as tetraester A hereinbelow). In the formula (1), if R has more than 12 carbon atoms, the manufacture of the fluorine-containing polyfunctional (meth)acrylate becomes difficult.

Preferred examples of diester A may include 1,8-bis((meth)acryloyloxy)-2,7-dihydroxy-4,4,5,5-tetrafluorooctane, 1,7-bis((meth)acryloyloxy)-2,8-dihydroxy-4,4,5,5-tetrafluorooctane, 2,7-bis((meth)acryloyloxy)-1,8-dihydroxy-4,4,5,5-tetrafluorooctane, 1,9-bis((meth)acryloyloxy)-2,8-dihydroxy-4,4,5,5,6,6-hexafluorononane, 1,8-bis((meth)acryloyloxy)-2,9-dihydroxy-4,4,5,5,6,6-hexafluorononane, 2,8-bis((meth)acryloyloxy)-1,9-dihydroxy-4,4,5,5,6,6-hexafluorononane, 1,10-bis((meth)acryloyloxy)- 2,9-dihydroxy-4,4,5,5,6,6,7,7-octafluorodecane, 1,9-bis((meth)acryloyloxy)-2,10-dihydroxy-4,4,5,5,6,6,7,7-octafluorodecane, 2,9-bis(meth)acryloyloxy)-1,10-dihydroxy-4,4,5,5,6,6,7,7-octafluorodecane, 1,11-bis((meth)acryloyloxy)-2,10-dihydroxy-4,4,5,5,6,6,7,7,8,8-decafluoroundecane, 1,10-bis((meth)acryloyloxy)-2,11-dihydroxy-4,4,5,5,6,6,7,7,8,8-decafluoroundecane, 2,10-bis((meth)acryloyloxy)-1,11-dihydroxy-4,4,5,5,6,6,7,7,8,8-decafluoroundecane, 1,12-bis((meth)acryloyloxy)-2,11-dihydroxy-4,4,5,5,6,6,7,7,8,8,9,9-dodecafluorododecane, 1,11-bis((meth)acryloyloxy)-2,12-dihydroxy-4,4,5,5,6,6,7,7,8,8,9,9-dodecafluorododecane, or 2,11-bis((meth)acryloyloxy)-1,12-dihydroxy-4,4,5,5,6,6,7,7,8,8,9,9-dodecafluorododecane.

Preferred examples of triester A may include 1,2,8-tris((meth)acryloyloxy)-7-hydroxy-4,4,5,5-tetrafluorooctane, 1,2,7-tris((meth)acryloyloxy)-8-hydroxy-4,4,5,5-tetraflouorooctane, 1,2,9-tris((meth)acryloyloxy)-8-hydroxy-4,4,5,5,6,6-hexafluorononane, 1,2,8-tris((meth)acryloyloxy)-9-hydroxy-4,4,5,5,6,6-hexafluorononane, 1, 2, 10-tris((meth)acryloyloxy)-9-hydroxy-4,4,5,5,6,6,7,7-octafluorodecane, 1,2,9-tris((meth)acryloyloxy)-10-hydroxy-4,4,5,5,6,6,7,7-octafluorodecane, 1, 2, 11-tris((meth)acryloyloxy)-10-hydroxy-4,4,5,5,6,6,7,7,8,8-decafluoroundecane, 1,2,10-tris((meth)acryloyloxy)-11-hydroxy-4,4,5,5,6,6,7,7,8,8-decafluoroundecane, 1,2,12-tris((meth)acryloyloxy)-11-hydroxy-4,4,5,5,6,6,7,7,8,8,9,9-dodecafluorododecane, or 1,2,11-tris((meth)

acryloyloxy)-12-hydroxy-4,4,5,5,6,6,7,7,8,8,9,9-dodecafluorododecane.

Preferred examples of tetraester A may include 4,4,5,5-tetrafluorooctane-1,2,7,8-tetraol tetra(meth)acrylate, 4,4,5,5,6,6-hexafluorononane-1,2,8,9-tetraol tetra(meth)acrylate, 4,4,5,5,6,6,7,7-octafluorodecane-1,2,9,10-tetraol tetra(meth)acrylate, 4,4,5,5,6,6,7,7,8,8-decafluoroundecane-1,2,10,11-tetraol tetra(meth)acrylate, or 4,4,5,5,6,6,7,7,8,8,9,9-dodecafluorododecane-1,2,11,12-tetraol tetra(meth)acrylate. The above mentioned diester A, triester A, and tetraester A may be used alone or as a mixture for use as a resin with low refractive index.

Diester A may be prepared by reacting diepoxide containing fluorine represented by the formula (2) (referred to as diepoxide B hereinbelow) and 0.8 to 5 equivalent of (meth) acrylic acid by ordinary ring opening reaction in the presence of a catalyst:

(2)

wherein R stands for a fluoroalkylene group having 2 to 12 carbon atoms and 2 or more fluorine atoms.

Triester A or tetraester A may be prepared, for example, by a two-step reaction including (a) reacting diepoxide B and 2 equivalent of (meth)acrylic acid by an ordinary ring-opening reaction in the presence of a catalyst to produce diester A, and (b) esterifying diester A with (meth) acryloylchloride.

Preferred examples of diepoxide B above may include 1,2-bis(2',3'-epoxypropyl)perfluoroethane, 1,3-bis(2',3'-epoxypropyl)perfluoropropane, 1,4-bis(2',3'-epoxypropyl)perfluorobutane, 1,5-bis(2',3'-epoxypropyl)perfluoropentane, or 1,6-bis(2',3'-epoxypropyl)perfluorohexane.

For reacting diepoxide B and (meth)acrylic acid in reaction (a), it is preferred to charge 1.6 to 10 mol, more preferably 2.0 to 3.6 mol of (meth)acrylic acid per 1 mol of diepoxide B. The temperature for the reaction is preferably 40 to 200° C., more preferably 80 to 120° C. The duration of the reaction is preferably 1 to 48 hours, more preferably 2 to 12 hours.

Examples of the catalyst used in reaction (a) may include tertiary amines such as triethylamine or benzyldimethylamine, or quaternary ammonium salts such as tetraethylammonium bromide or tetramethylammonium bromide. The amount of the catalyst is preferably 0.001 to 5.0% by weight, more preferably 0.01 to 2.5% by weight of the total weight of the reaction mixture.

In reaction (a), it is preferred to add a polymerization inhibitor for inhibiting polymerization during the reaction, such as hydroquinone, hydroquinone monoethyl ether or tert-butylcatechol. The amount of the polymerization initiator is preferably 0.001 to 2.0% by weight, more preferably 0.005 to 0.2% by weight of the total weight of the reaction mixture.

After the completion of reaction (a), the resulting mixture containing diester A maybe subjected to a variety of treatments depending on the need to obtain diester A of high quality, or the resulting mixture containing diester A may also be subjected to a variety of treatments depending on the need before it is subjected to step (b) for preparing triester A or tetraester A. Examples of such treatments may include dissolving the reaction mixture in chloroform, methylene chloride, or trifluoromethylbenzene followed by washing with an alkaline aqueous solution such as sodium hydroxide or sodium carbonate for removing excess (meth)acrylic acid, excess polymerization inhibitor, or the catalyst. The treatment may optionally be followed by purification, for example by vacuum distillation. In the vacuum distillation, it is preferred to add a polymerization initiator such as hydroquinone, hydroquinone monoethyl ether, or tert-butylcatechol to the distillation system for inhibiting polymerization. The amount of the polymerization initiator is preferably 0.001 to 2.0% by weight, more preferably 0.005 to 0.2% by weight of the total weight of the reaction mixture.

Diester A obtained through reaction (a) is a mixture of three kinds of isomers represented by the formulae (3) to (5) below, wherein $R^5$ stands for a (meth)acryloyl group and R is the same as R in diepoxide B. The isomers in the mixture may be used as a mixture or used after separation.

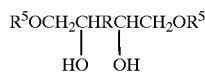
(3)

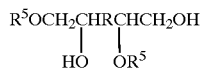
(4)

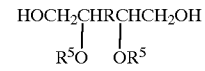
(5)

The mixing ratio of diester A and (meth)acryloylchloride in reaction (b) is preferably 0.8 to 3 mol, more preferably 1.0 to 2.0 mol of (meth)acryloylchloride per 1 mol of diester A for preparing triester A, and preferably 1.6 to 10 mol, more preferably 2.0 to 4.0 mol of (meth)acryloylchloride per 1 mol of diester A for preparing tetraester A.

In reaction (b), base such as tertiary alkylamine, for example, triethylamine or benzyldimethylamine or pyridine may be added for capturing hydrochloric acid generated during the reaction. The amount of the base is preferably 0.8 to 3.0 mol per 1 mol of diester A for preparing triester A, and preferably 1.6 to 10.0 mol, more preferably 2.0 to 4.5 mol per 1 mol of diester A for preparing tetraester A.

It is preferred to proceed with reaction (b) in a suitable solvent. Examples of such a solvent may include chloroform, methylene chloride, or trifluoromethylbenzene. The amount of the solvent is preferably 20 to 2000 parts by weight, more preferably 100 to 500 parts by weight based on 100 parts by weight of the mixture of diester A, (meth)acryloylchloride, and the base optionally added.

The temperature for reaction (b) is preferably −20 to 20° C., more preferably −10 to 10° C., and the duration of reaction (b) is preferably 0.1 to 12 hours, more preferably 0.5 to 2 hours.

After the completion of reaction (b), the resulting mixture of triester A or tetraester A, unreacted components, byproducts, chloride of the capturing agent, and the solvent may be subjected to a variety of treatments depending on the need to obtain the desired triester A or tetraester A. Such treatments may include adding a small amount of alcohols such as methanol or ethanol or water to the mixture for decomposing the excess (meth)acryloylchloride in the reaction system, washing the mixture with an acid aqueous solution such as diluted hydrochloric acid, or purifying the mixture by vacuum distillation or column chromatography. In the vacuum distillation, it is preferred to add a polymerization inhibitor such as hydroquinone, hydroquinone monoethyl ether, or tert-butylcatechol to the mixture for inhibiting polymerization. The amount of the polymerization inhibitor is preferably 0.001 to 2.0% by weight, more preferably 0.005 to 0.2% by weight of the total weight of the mixture resulting from the reaction and the polymerization inhibitor.

Triester A obtained through the reaction (b) is a mixture of two kinds of isomers represented by the formulae (6) and (7) below, wherein $R^5$ is the same as $R^5$ mentioned above. The isomers in the mixture may be used as the mixture or after separation for various usage.

 (6)

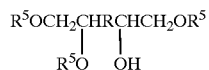 (7)

The fluorine-containing polyfunctional (meth)acrylate of the present invention may be cured by cross-linking to produce a cured film having excellent abrasion resistance and adhesion, and may be used alone or as a mixture. Specifically, diester A, triester A, tetraester A, or the mixtures thereof may be used.

The monomer composition of the present invention contains the fluorine-containing polyfunctional (meth)acrylate selected from the group consisting of diester A, triester A, tetraester A, each represented by the formula (1), or the mixtures thereof (sometimes collectively referred to as polyfunctional ester A hereinbelow).

The content of polyfunctional ester A is 5 to 100% by weight, preferably 10 to 100% by weight of the total weight of the composition. When the monomer composition of the present invention is cured by polymerization, it is cross-linked to acquire three-dimensional net work structure, thereby giving a cured film having excellent abrasion resistance, adhesion, wear resistance, heat resistance, and weatherability.

Preferred examples of polyfunctional ester A may include the examples of diester A, triester A, tetraester A mentioned above, or the mixtures thereof.

The monomer composition of the present invention may optionally contain preferably less than 95% by weight, more preferably less than 90% by weight other curing materials such as ordinary thermosetting monomers or energy-beam curable monomers. Preferred examples of the thermosetting monomers and energy-beam curable monomers may include polyfunctional monomers having two or more polymerizable unsaturated groups, for example, polyalkylene glycol di(meth)acrylate such as dipentaerythritol hexa(meth)acrylate, dipentaerythritol penta(meth)acrylate, dipentaerythritol tetra(meth)acrylate, pentaerythritol tetra(meth)acrylate, pentaerythritol tri(meth)acrylate, pentaerythritol di(meth)acrylate, ditrimethylolpropane tetra(meth)acrylate, ditrimethylolpropane tri(meth)acrylate, ditrimethylolpropane di(meth)acrylate, trimethylolpropane tri(meth)acrylate, trimethylolpropane di(meth)acrylate, tetramethylolmethane tetraacrylate, 1,1,1-tris(acryloyloxyethoxyethoxy)propane, 2,2-bis(4-acryloyloxyethoxyethoxyphenyl)propane, 2,2-bis(4-acryloyloxyethoxyethoxycyclohexyl)propane, 2,2-bis(4-acryloyloxyethoxyphenyl)methane, neopentyl glycol di(meth)acrylate, hydrogenated dicyclopentadienyl di(meth)acrylate, tris(hydroxyethyl)isocyanurate triacrylate, tris(hydroxyethyl)isocyanurate diacrylate, 1,4-butanediol di(meth)acrylate, 1,6-hexanediol di(meth)acrylate, isobornyl di(meth)acrylate, polyethylene glycol di(meth)acrylate, polypropylene glycol di(meth)acrylate, or polytetramethylene glycol di(meth)acrylate. These may be used alone or as a mixture.

The monomer composition of the present invention may optionally contain monofunctional (meth)acrylate as long as the desired effect of the present invention is not deteriorated. Such monofunctional (meth)acrylate may preferably be fluorine-containing monofunctional (meth)acrylate in view of the purpose of lowering the refractive index of the monomer composition, such as 2,2,2-trifluoroethyl (meth)acrylate, 2,2,3,3,3-pentafluoropropyl (meth)acrylate, 2,2,3,3,4,4,4-heptafluorobutyl (meth)acrylate, 2,2,3,3,4,4,5,5,5-nonafluoropentyl (meth)acrylate, 2,2,3,3,4,4,5,5,6,6,6-undecafluorohexyl (meth)acrylate, 2,2,3,3,4,4,5,5,6,6,7,7,7-tridecafluoroheptyl (meth)acrylate, 2,2,3,3,4,4,5,5,6,6,7,7,8,8,8-pentadecafluorooctyl (meth)acrylate, 3,3,4,4,5,5,6,6,7,7,8,8,8-tridecafluorooctyl (meth)acrylate, 2,2,3,3,4,4,5,5,6,6,7,7,8,8,9,9,10,10,10-nonadecafluorodecyl (meth)acrylate, 3,3,4,4,5,5,6,6,7,7,8,8,9,9,10,10,10-heptadecafluorodecyl (meth)acrylate, 2-trifluoromethyl-3,3,3-trifluoropropyl (meth)acrylate, 3- trifluoromethyl- 4,4,4-trifluorobutyl (meth)acrylate, 1-methyl-2,2,3,3-pentafluoropropyl (meth)acrylate, or 1-methyl-2,2,3,3,4,4,4-heptafluorobutyl (meth)acrylate. These may be used alone or as a mixture.

The monomer composition of the present invention may also contain, if necessary, fluorine-containing bifunctional (meth)acrylate other than diester A as a curing material as long as the desired effect of the present invention is not deteriorated. Preferred examples of the fluorine-containing bifunctional (meth)acrylate other than diester A may include 2,2,2-trifluoroethylethylene glycol di(meth)acrylate, 2,2,3,3,3-pentafluoropropylethylene glycol di(meth)acrylate, 2,2,3,3,4,4,4-heptafluorobutylethylene glycol di(meth)acrylate, 2,2,3,3,4,4,5,5,5-nonafluoropentylethylene glycol di(meth)acrylate, 2,2,3,3,4,4,5,5,6,6,6-undecafluorohexylethylene glycol di(meth)acrylate, 2,2,3,3,4,4,5,5,6,6,7,7,7-tridecafluoroheptylethylene glycol di(meth)acrylate, 2,2,3,3,4,4,5,5,6,6,7,7,8,8,8-pentadecafluorooctylethylene glycol di(meth)acrylate, 2,2,3,3,4,4,5,5,6,6,7,7,8,8,9,9,10,10,10-nonadecafluorodecylethylene glycol di(meth)acrylate, 2,2,3,3-tetrafluorobutanediol di(meth)acrylate, 2,2,3,3,4,4-hexafluoropentadiol di(meth)acrylate, 2,2,3,3,4,4,5,5-octafluorohexanediol di(meth)acrylate, 2,2,3,3,4,4,5,5,6,6-decafluoroheptanediol di(meth)acrylate, 2,2,3,3,4,4,5,5,6,6,7,7-dodecafluorooctanediol di(meth)acrylate, 2,2,3,3,4,4,5,5,6,6,7,7,8,8-tetradecafluorononanediol di(meth)acrylate, 2,2,3,3,4,4,5,5,6,6,7,7,8,8,9,9-hexadecafluorodecanediol di(meth)acrylate, 2,2,3,3,4,4,5,5,6,6,7,7,8,8,9,9,10,10-octadecafluoroundecanediol di(meth)acrylate, or 2,2,3,3,4,4,5,5,6,6,7,7,8,8,9,9,10,10,11,11-eicosafluorododecanediol di(meth)acrylate. These may be used alone or as a mixture.

The monomer composition of the present invention may optionally contain less than 95% by weight, preferably less than 90% by weight inorganic powders. There is no particular limitation to the inorganic powders, but inorganic powders having the refractive index of 1.5 or lower such as magnesium fluoride or colloidal silica are particularly preferred in order not to increase the refractive index of the overall composition. The particle size of the powders is preferably sufficiently smaller than the wave length of the visible radiation for the purpose of ensuring the transparency of the low refractivity material. Specifically, the particle size is preferably not larger than 100 nm, more preferably not larger than 50 nm.

The monomer composition of the present invention may optionally be mixed with a polymer for improving the film forming property. The polymer to be added is not particularly limited, but preferably a polymer of fluorine-containing (meth)acrylate, or a copolymer of fluorine-containing (meth) acrylate with other monomers. The mixing ratio of the polymer is preferably 25 parts by weight or less, more preferably 10 parts by weight or less based on 100 parts by weight of the curing materials in the monomer composition.

The low refractivity material of the present invention is prepared by curing the monomer composition by polymerization, and has the refractive index of 1.49 or lower, more preferably 1.35 to 1.49.

The curing by polymerization may be carried out by optionally admixing a curing initiator and/or a solvent such as isopropylalcohol or toluene to the monomer composition; applying the resulting mixture to a substrate such as a transparent substrate by an ordinary coating method such as roll coating method, gravure coating method, dip coating method, or spin coating method; drying; and curing by heating or irradiating active energy beam such as ultraviolet ray, electron beam, or radio active ray. The conditions for curing by polymerization may suitably be selected depending on the curing materials in the composition. When the low refractivity material is formed into a film, the film thickness may suitably be selected depending on the purpose.

Examples of the curing initiator may include azo radical polymerization initiators such as azobisisobutyronitrile, azobiscyclohexanecarbonitrile, or azobisvaleronitrile; radical polymerization initiators of organic peroxide type such as benzoyl peroxide, tert-butylhydroperoxide, cumene peroxide, or diacylperoxide, photopolymerization initiators such as benzoin compounds including benzoin, benzoin methyl ether, benzoin ethyl ether, or benzoin isopropyl ether, carbonyl compounds including benzyl, benzophenone, acetophenone, or Michler's ketone, azo compounds including azobisisobutyronitrile or azodibenzoyl, or a mixture of α-diketone and a tertiary amine. The amount of the curing initiator may be 0.01 to 10% by weight of the total weight of the curing materials in the monomer composition and the curing initiator.

The reflection reducing film of the present invention has a transparent substrate and a layer of the low refractivity material. The layer of the low refractivity material preferably has a suitable thickness. The suitable thickness is preferably selected so that the wave length which indicated the minimum reflectance of the reflection reducing film is usually 420 to 720 nm, more preferably 520 to 620 nm.

The kind of the transparent substrate is not particularly limited as long as the substrate is transparent. Usually, a PET (polyethylene terephthalate) film, a TAC (triacetyl cellulose) film, an acryl film, or a polycarbonate film may be used.

The reflection reducing film of the present invention may be composed of the transparent substrate and the layer of the low refractivity material, or of the transparent substrate, the layer of the low refractivity material, and at least one material layer therebetween. The material layer may be a layer of a high refractivity material for improving the reflection reducing effect. The layer of the high refractivity material preferably has the refractive index of 1.55 or higher, and the thickness of the layer may preferably be selected so that the wave length which indicated the maximum reflectance of the film provided with the layer of the high refractivity material is usually 400 to 900 nm.

The transparent substrate may be provided with one layer of the low refractivity material and one layer of the high refractivity material, or it may be provided with two or more layers of each material. When two or more layers of each material are provided, the layers of the low refractivity material and the high refractivity material may be laminated alternately, with the outermost layer being of the low refractivity material. When two or more layers of each material are provided, each layer of the low refractivity material or the high refractivity material may be made of the same or different materials.

The layer of the low refractivity material may be formed by optionally admixing a curing initiator and/or a solvent such as isopropylalcohol or toluene to the fluorine-containing monomer composition; applying the resulting mixture to a substrate such as a transparent substrate by an ordinary coating method such as roll coating method, gravure coating method, dip coating method, or spin coating method; drying; and curing by heating or irradiating active energy beam such as ultraviolet ray, electron beam, or radio active ray. The conditions for curing by polymerization may suitably be selected depending on the curing materials in the composition. The layer of the high refractivity material may be formed in the same way.

The reflection reducing film of the present invention may be provided with a hard coating for further improving the abrasion resistance of the reflection reducing film. The hard coating may be provided between the laminated layers of the low refractivity material and the high refractivity material and the transparent substrate. The kind of the hard coating is not particularly limited, and may be made of an ordinary resin for hard coating prepared from the polyfunctional monomer having two or more polymerizable unsaturated groups. However, if the difference in the refractive index of the transparent substrate and the hard coating is too large, reflection will occur at the interface therebetween. Thus, the difference in the refractive index of the transparent substrate and the hard coating is preferably kept as small as possible. The thickness of the hard coating is preferably 1 to 10 $\mu$m, more preferably 3 to 5 $\mu$m. The method of forming the hard coating is not particularly limited, and may include applying the hard coating material to a substrate such as a transparent substrate by an ordinary coating method such as roll coating method, gravure coating method, dip coating method, or spin coating method, drying, and curing by an ordinary method using energy beam or heat.

Since the fluorine-containing polyfunctional (meth) acrylate of the preset invention has a plurality of (meth) acryloyl groups, it is cured by cross-linking polymerization to acquire three-dimensional net work structure, and gives a cured film having high surface hardness and excellent abrasion resistance, wear resistance, heat resistance, and weatherability. Further, diester A and triester A having a hydroxyl group can improve the adhesion of the cured coating film. The obtained cured product has superior light transmittance and low refractive index as well as excellent adhesion, so that it is useful as a resin with low refractive index for antireflection coatings or clad materials for optical fibers which requires superior abrasion resistance and adhesion.

Since the monomer composition of the present invention contains the particular fluorine-containing polyfunctional (meth)acrylate, the cured product prepared by polymerizing the monomer composition has the properties of both the low refractive index and the hardness of (meth)acrylate, and the monomer composition can be formed into a film by applying on a substrate and cured by polymerization, thereby preparing the low refractivity material of the present invention. The low refractivity material of the present invention has the properties of both the low refractive index and the hardness of (meth)acrylate, and has low refractive index and high surface hardness. Further, since it is prepared from diester A or triester A having a hydroxyl group, its adhesion to other materials is further improved.

The reflection reducing film of the present invention is provided with a layer of the low refractivity material, it has low refractive index, high surface hardness, and high adhesion, and may be applied to a variety of usage. Accordingly, by using the monomer composition of the present invention, reflection reducing films having a large area of a layer of the low refractivity material may be produced continuously and effectively at a low cost, compared to the conventional vapor deposition of magnesium fluoride.

EXAMPLES

The present invention will now be explained with reference to Examples and Comparative Examples, but the present invention is not limited thereto.

Example 1-1

Into a reactor equipped with a stirrer, a cooling tube and a gas introducing tube, 314.2 g (1 mol) of. 1,4-bis(2',3'-epoxypropyl)perfluorobutane, 216.2 g (3 mol) of acrylic acid, 4.4 g of tetraethylammoniumide, and 0.44 g of tert-butylcatechol were charged, gradually heated up to 95 to 100° C. in an oil bath, stirred at this temperature for 4 hours, and then cooled down to the room temperature. The resulting reaction liquid was dissolved in 500 ml of chloroform, and the solution thus obtained was washed three times with a 10% aqueous solution of sodium carbonate, and three times with saturated brine. Chloroform was removed from the washed solution under reduced pressure to obtain yellow crystals. The yellow crystals were subjected to purification by column chromatography using a mixed solvent of ethyl acetate/n-hexane (volume ratio 1:2) as a developing solvent, thereby obtaining 417.1 g (0.91 mol) of product A. Product A was a compound having the structure represented by the formula (8):

$XCH_2(CF_2)_4CH_2X$ (8)

wherein two X's are the same or different groups, and are group $X^1$ represented by the formula (9) or group $X^2$ represented by the formula (10). Product A was a mixture of three kinds of isomers, namely the isomer having two $X^1$'s, the isomer having two $X^2$'s, and the isomer having one $X^1$ and one $X^2$.

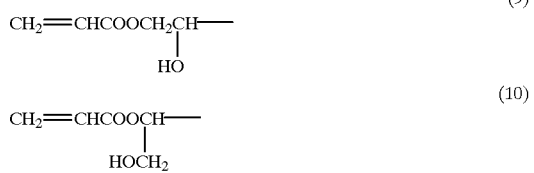

The results of $^1$H-NMR, $^{19}$F-NMR, and Exact MS of the compound thus obtained are shown below.

$^1$H-NMR (δ (ppm) CDCl$_3$/TMS); $X^1$: 6.47(dd, 1H); 6.17 (dd, 1H); 5.91 (dd, 1H); 4.50–4.38 (m, 1H), 4.30,4.20 (dABq, 2H), 2.45 (d, 1H); $X^2$: 6.42 (dd, 1H), 6.14 (dd, 1H), 5.86 (dd, 1H), 5.48–5.39 (m, 1H), 3.82–3.76 (m, 2H), 2.76 (t, 1H); From the ratio of intensity, $X^1$:$X^2$=85:15 $XC\underline{H}_2CF_2$—: 2.73–2.28 (m, 2H); $^{19}$F-NMR (δ (ppm) CDCl$_3$/CFCl$_3$): −110.20, −120.44; Exact MS: Measured value, 458.0985; Theoretical value, $C_{16}H_{18}F_8O_6$: 458.0976.

Example 1-2

312.2 g (0.87 mol) of product B having the structure represented by the formula (11) was prepared in the same way as in Example 1-1 except that 314.2 g (1 mol) of 1,4-bis(2'3'-epoxypropyl)perfluorobutane was replaced by 214.2 g (1 mol) of 1,2-bis(2',3'-epoxypropyl) perfluoroethane.

$XCH_2(CF_2)_2CH_2X$ (11)

wherein two X's are the same or different groups, and are $X^1$ or $X^2$ above. Product B was a mixture of three kinds of isomers, namely the isomer having two $X^1$'s, the isomer having two $X^2$'s, and the isomer having one $X^1$ and one $X^2$.

The results of $^1$H-NMR, $^{19}$F-NMR, and Exact MS of the compound thus obtained are shown below.

$^1$H-NMR (δ (ppm) CDCl$_3$/TMS); $X^1$: 6.46 (dd, 1H), 6.17 (dd, 1H), 5.91 (dd, 1H), 4.50–4.38 (m, 1H), 4.29, 4.19 (dABq, 2H), 2.45 (d, 1H); $X^2$: 6.42 (dd, 1H), 6.14 (dd, 1H), 5.86 (dd, 1H), 5.47–5.39 (m, 1H), 3.81–3.76 (m, 2H), 2.75 (t, 1H); From the ratio of intensity, $X^1$:$X^2$=85:15; $XC\underline{H}_2CF_2$—: 2.72–2.27 (m, 2H); $^{19}$F-NMR (δ (ppm) CDCl$_3$/CFCl$_3$): −109.62; Exact MS: Measured value, 358.1034; Theoretical value, $C_{14}H_{18}F_4O_6$: 358.1039.

Example 1-3

502.3 g (0.90 mol) of product C having the structure represented by the formula (12) was prepared in the same way as in Example 1-1 except that 314.2 g (1 mol) of 1,4-bis(2'3'-epoxypropyl)perfluorobutane was replaced by 414.2 g (1 mol) of 1,6-bis(2'3'-epoxypropyl) perfluorohexane.

$XCH_2(CF_2)_6CH_2X$ (12)

wherein two X's are the same or different groups, and are $X^1$ or $X_2$ above. Product C was a mixture of three kinds of isomers, namely the isomer having two $X^1$'s, the isomer having two $X^2$'s, and the isomer having one $X^1$ and one $X^2$.

The results of $^1$H-NMR, $^{19}$F-NMR, and Exact MS of the compound thus obtained are shown below.

$^1$H-NMR (δ (ppm) CDCl$_3$/TMS); $X^1$: 6.47 (dd, 1H), 6.18 (dd, 1H), 5.91 (dd, 1H), 4.51–4.38 (m, 1H), 4.30,4.21 (dABq,2H), 2.45 (d, 1H); $X^2$: 6.42 (dd, 1H), 6.15 (dd, 1H), 5.86 (dd, 1H), 5.48–5.40 (m, 1H), 3.82–3.76 (m, 2H), 2.77 (t, 1H); From the ratio of intensity, $X^1$:$X^2$=85:15; $XC\underline{H}_2CF_2$—: 2.74–2.28 (m, 2H); $^{19}$F-NMR (δ (ppm) CDCl$_3$/CFCl$_3$): −112.42,−121.44,−123.18; Exact MS: Measured value 558.0917; Theoretical value, $C_{18}H_{18}F_{12}O_6$: 558.0912.

Example 2-1

Into a reactor equipped with a stirrer, a cooling tube, and a gas introducing tube, 314.2 g (1 mol) of 1,4-bis(2',3'-epoxypropyl)perfluorobutane, 216.2 g (3 mol) of acrylic acid, 4.4 g of tetraethylammonium bromide, and 0.44 g of tert-butylcatechol were charged, gradually heated up to 95 to 100° C. in an oil bath, stirred at this temperature for 4 hours, and then cooled down to the room temperature. The resulting reaction liquid was dissolved in 500 ml of chloroform, and the solution thus obtained was washed three times with a 10% aqueous solution of sodium carbonate, and three times with saturated brine. It is believed that the chloroform solution thus obtained contains the compounds represented by the formulae (13), (14), and (15).

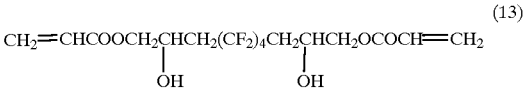

-continued

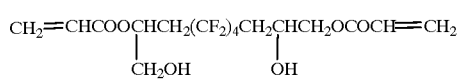
(14)

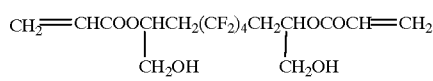
(15)

Into a reactor of 5 liter capacity equipped with a stirrer, a thermometer, a gas introducing tube, and a dropping funnel, the above chloroform solution and 152 g (1.5 mol) of triethylamine were charged. 136 g (1.5 mol) of acryloyl-chloride was dissolved in 150 ml of chloroform under ice cooling, and the obtained solution was added dropwise to the starting mixture from the dropping funnel, while the temperature of the reaction liquid was kept under 5° C. under ice cooling.

After the completion of dropping, the reaction liquid was stirred for 2 hours under ice cooling, and 30 ml of methanol was added to the reaction liquid, followed by stirring for 10 minutes. Chloroform was removed from the obtained liquid under reduced pressure to obtain yellow crystals. The yellow crystals were subjected to purification by column chromatography using a mixed solvent of ethyl acetate/n-hexane (volume ratio 1:4) as a developing solvent, followed by removal of the solvents under reduced pressure, thereby obtaining 102.5 g (0.20 mol) of the target product D. Product D was a mixture of product $D^1$ represented by the formula (16) and product $D^2$ represented by the formula (17). From the ratio of intensity in $^1$H-NMR, it was revealed that the ratio of product $D^1$ to product $D_2$ was 85:15. The results of $^1$H-NMR, $^{19}$F-NMR, and Exact MS of the compound thus obtained are shown below.

(Product $D^1$)

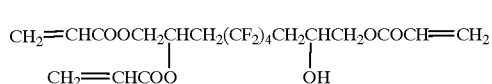
(16)

$^1$H-NMR (δ (ppm) CDCl3/TMS), 6.47 (dd, 1H), 6.44 (dd, 1H), 6.44 (dd, 1H), 6.17 (dd, 1H), 6.15 (dd, 1H), 6.11 (dd, 1H), 5.91 (dd, 1H), 5.91 (dd, 1H), 5.87 (dd, 1H), 5.64–5.60 (m, 1H), 4.50–4.38 (m, 1H), 4.42,4.27 (dABq, 2H), 4.30, 4.20 (dABq, 2H), 2.73–2.28 (m, 4H), 2.45 (d, 1H); $^{19}$F-NMR (δ (ppm) CDCl$_3$/CFCl$_3$): −110.20,−120.44; Exact MS: Measured value, 512.1399; Theoretical value, $C_{19}H_{20}F_8O_7$: 512.1395.

(Product $D^2$)

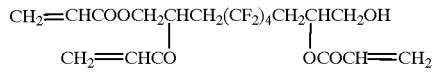
(17)

$^1$H-NMR (δ (ppm) CDCl$_3$/TMS), 6.44 (dd, 1H), 6.44 (dd, 1H), 6.42 (dd, 1H), 6.15 (dd, 1H), 6.14 (dd, 1H), 6.11 (dd, 1H), 5.91 (dd, 1H), 5.87 (dd, 1H), 5.86 (dd, 1H), 5.64–5.60 (m, 1H), 5.48–5.39 (m, 1H), 4.42,4.27 (dABq, 2H), 3.82–3.76 (m, 2H), 2.76 (t, 1H), 2.73–2.28 (m, 4H).

Example 2-2

78.3 g (0.19 mol) of product E was prepared in the same way as in Example 2-1 except that 314.2 g (1 mol) of 1,4-bis(2',3'-epoxypropyl)perfluorobutane was replaced by 214.2 g (1 mol) of 1,2-bis(2',3'-epoxypropyl) perfluoroethane. Product E was a mixture of product $E^1$ represented by the formula (18) and product $E^2$ represented by the formula (19). From the ratio of intensity in $^1$H-NMR, it was revealed that the ratio of product $E^1$ to product $E^2$ was 85:15. The results of $^1$H-NMR, $^{19}$F-NMR, and Exact MS of the compound thus obtained are shown below.

(Product $E^1$)

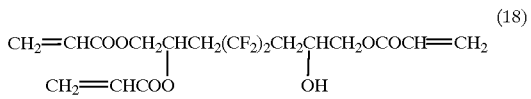
(18)

$^1$H-NMR (δ (ppm) CDCl$_3$/TMS), 6.46 (dd, 1H), 6.44 (dd, 1H), 6.42 (dd, 1H), 6.17 (dd, 1H), 6.14 (dd, 1H), 6.11 (dd, 1H), 5.91 (dd, 1H), 5.91 (dd, 1H), 5.87 (dd, 1H), 5.64–5.60 (m, 1H), 4.50–4.38 (m, 1H), 4.42,4.27 (dABq, 2H), 4.29, 4.19 (dABq, 2H), 2.7 2–2.28 (m, 4H), 2.45 (d, 1H); $^{19}$F-NMR (δ (ppm) CDCl$_3$/CFCl$_3$): −109.62; Exact MS: Measured value, 412.1154; Theoretical value, $C_{17}H_{20}F_4O_7$: 412.1145.

(Product $E^2$)

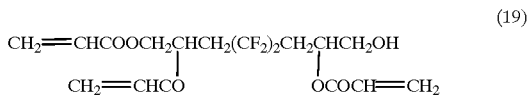
(19)

$^1$H-NMR (δ (ppm) CDCl$_3$/TMS), 6.44 (dd, 1H), 6.44 (dd, 1H), 6.42 (dd, 1H), 6.14 (dd, 1H), 6.14 (dd, 1H), 6.11 (dd, 1H), 5.91 (dd, 1H), 5.87 (dd, 1H), 5.86 (dd, 1H), 5.64–5.60 (m, 1H), 5.48–5.39 (m, 1H), 4.42,4.27 (dABq, 2H), 3.81–3.76 (m, 2H), 1.75 (t, 2H), 2.72–2.27 (m, 4H).

Example 2-3

128.6 g (0.21 mol) of product F was prepared in the same way as in Example 2-1 except that 314.2 g of 1,4-bis(2',3'-epoxypropyl)perfluorobutane was replaced by 414.2 g (1 mol) of 1,6-bis(2',3'-epoxypropyl)perfluorohexane. Product F was a mixture of product $F^1$ represented by the formula (20) and product $F^2$ represented by the formula (21). From the ratio of intensity in $^1$H-NMR, it was revealed that the ratio of product $F^1$ toproduct $F^2$ was 85:15. The results of $^1$H-NMR, $^{19}$F-NMR, and Exact MS of the compound thus obtained are shown below.

(Product $F^1$)

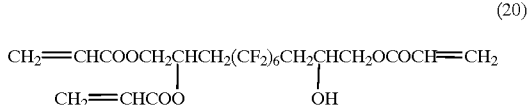
(20)

$^1$H-NMR (δ (ppm) CDCl$_3$/TMS), 6.47 (dd, 1H), 6.44 (dd, 1H), 6.44 (dd, 1H), 6.18 (dd, 1H), 6.15 (dd, 1H), 6.11 (dd, 1H), 5.91 (dd, 1H), 5.91 (dd, 1H), 5.87 (dd, 1H), 5.64–5.60 (m, 1H), 4.51–4.38 (m, 1H), 4.42,4.27 (dABq, 2H), 4.30, 4.21 (dABq, 2H), 2.7 4–2.28 (m, 4H), 2.45 (d, 1H); $^{19}$F-NMR (δ (ppm) CDCl$_3$/CFCl$_3$): −112.42,−121.44,−123.18;

Exact MS: Measured value, 612.1011; Theoretical value, $C_{21}H_{20}F_{12}O_7$: 612.1017.
(Product $F^2$)

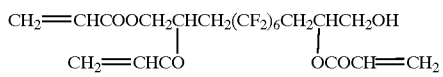
(21)

$^1$H-NMR (δ (ppm) CDCl$_3$/TMS), 6.44 (dd, 1H), 6.44 (dd, 1H), 6.42 (dd, 1H), 6.15 (dd, 1H), 6.14 (dd, 1H), 6.11 (dd, 1H), 5.91 (dd, 1H), 5.87 (dd, 1H), 5.86 (dd, 1H), 5.64–5.60 (m, 1H), 5.48–5.40 (m, 1H), 4.42,4.27 (dABq, 2H), 3.82–3.76 (m, 2H), 2.77 (t, 1H), 2.74–2.28 (m, 4H).

Example 3-1

Into a reactor equipped with a stirrer, a cooling tube, and a gas introducing tube, 314.2 g (1 mol) of 1,4-bis(2',3'-epoxypropyl)perfluorobutane, 216.2 g (3 mol) of acrylic acid, 4.4 g of tetraethylammonium bromide, and 0.44 g of tert-butylcatechol were charged, gradually heated up to 95 to 100° C. in an oil bath, stirred at this temperature for 4 hours, and then cooled down to the room temperature. The resulting reaction liquid was dissolved in 500 ml of chloroform, and the solution thus obtained was washed three times with a 10% aqueous solution of sodium carbonate, and three times with saturated brine. It is believed that the chloroform solution thus obtained contains the compounds represented by the formulae (13), (14), and (15) above.

Into a reactor of 5 liter capacity equipped with a stirrer, a thermometer, a gas introducing tube, and a dropping funnel, the above chloroform solution and 607.2 g of triethylamine were charged. 362 g (4 mol) of acryloylchloride was dissolved in 300 ml of chloroform under ice cooling, and the obtained solution was added dropwise to the startingmixture from the dropping funnel, while the temperature of the reaction liquid was kept under 5° C. under ice cooling. After the completion of dropping, the reaction liquid was stirred for 2 hours under ice cooling, and 80 ml of methanol was added to the reaction liquid, followedby stirring for 10 minutes. Chloroform was removed from the obtained liquid under reduced pressure to obtain yellow crystals. The yellow crystals were subjected to purification by column chromatography using a mixed solvent of ethyl acetate/n-hexane (volume ratio 1:4) as a developing solvent, followed by removal of the solvents under reduced pressure, thereby obtaining 134.6 g (0.24 mol) of product G (4,4,5,5,6,6,7,7-octafluorodecane-1,2,9,10-tetraol tetraacrylate) represented by the formula (22).

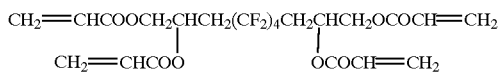
(22)

The results of $^1$H-NMR, $^{19}$F-NMR, and Exact MS of the compound thus obtained are shown below.

$^1$H-NMR (δ (ppm) CDCl$_3$/TMS), 6.44 (dd, 1H), 6.44 (dd, 1H), 6.15 (dd, 1H), 6.11 (dd, 1H), 5.91 (dd, 1H), 5.87 (dd, 1H), 5.64–5.60 (m, 1H), 4.42,4.27 (dABq, 2H), 2.63–2.50 (m, 1H); $^{19}$F-NMR (δ (ppm) CDCl$_3$/CFCl$_3$): –110.21,–120.44; Exact MS: Measured value, 566.1195; Theoretical value, $C_{22}H_{22}F_8O_8$: 566.1187.

Example 3-2

105.4 g (0.22 mol) of product H (4,4,5,5-tetrafluorooctane-1,2,7,8-tetraol tetraacrylate) represented by the formula (26) was prepared in the same way as in Example 3-1 via the compounds represented by the formulae (23), (24), and (25), except that 314.2 g (1 mol) of 1,4-bis(2',3'-epoxypropyl)perfluorobutane was replaced by 214.2 g (1 mol) of 1,2-bis(2',3'-poxypropyl)perfluoroethane.

(23)

(24)

(25)

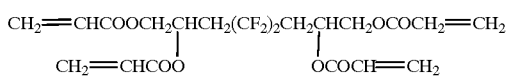
(26)

The results of $^1$H-NMR, $^{19}$F-NMR, and Exact MS of the compound thus obtained are shown below.

$^1$H-NMR (δ (ppm) CDCl$_3$/TMS), 6.45 (dd, 1H), 6.44 (dd, 1H), 6.16 (dd, 1H), 6.11 (dd, 1H), 5.92 (dd, 1H), 5.87 (dd, 1H), 5.65–5.61 (m, 1H), 4.42,4.28 (dABq, 2H), 2.63–2.51 (m, 1H); $^{19}$F-NMR (δ (ppm) CDCl$_3$/CFCl$_3$), –109.63; Exact MS: Measured value, 466.1244; Theoretical value, $C_{20}H_{22}F_4O_8$: 466.1251.

Example 3-3

159.9 g (0.24 mol) of product I (4,4,5,5,6,6,7,7,8,8,9,9-dodecafluorododecane-1,2,11,12-tetraol tetraacrylate) represehted by the formula (30) was prepared in the same way as in Example 3-1 via the compounds represented by the formulae (27), (28), and (29) except that 314.2 g (1 mol) of 1,4-bis(2',3'-epoxypropyl)perfluorobutane was replaced by 414.2 g (1 mol) of 1,6-bis(2',3'-epoxypropyl) perfluorohexane.

(27)

(28)

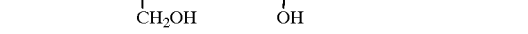
(29)

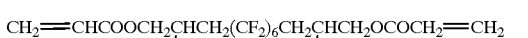
(30)

The results of $^1$H-NMR, $^{19}$F-NMR, and Exact MS of the compound thus obtained are shown below.

$^1$H-NMR (δ (ppm) CDCl$_3$/TMS), 6.44 (dd, 1H), 6.43 (dd, 1H), 6.15 (dd, 1H), 6.10 (dd, 1H), 5.91 (dd, 1H), 5.86 (dd, 1H), 5.64–5.99 (m, 1H), 4.41,4.27 (dABq, 2H), 2.63–2.49 (m, 1H); $^{19}$F-NMR (δ (ppm) CDCl$_3$/CFCl$_3$) –112.41,–121.44,–123.16; Exact MS: Measured value, 666.1114; Theoretical value, C$_{24}$H$_{22}$F$_{12}$O$_8$: 666.1123.

Preparation Exmaple 1

45 parts by weight of dipentaerythritol hexaacrylate manufactured by HITACHI CHEMICAL CO., LTD., 30 parts by weight of polyethylene glycol diacrylate (trade name "A-400", manufactured by SHIN-NAKAMURA CHEMICAL CO., LTD.), 4 parts by weight of "IRGACURE 184" (trade name, manufactured by CIBA GEIGY LTD.) as a curing initiator, and 20 parts by weight of isopropyl alcohol as a solvent were mixed together, and the obtained mixture was applied to a PET film by a micro gravure coater manufactured by YASUISEIKI CO., LTD. so that the film thickness was 5 μm. The film was cured by irradiating the film with ultraviolet ray by an ultraviolet irradiator manufactured by IWASAKI ELECTRIC CO., LTD. at 800 mJ/cm$^2$ to form a hard coating, thereby preparing a PET film with hard coating (abbreviated as HC-PET hereinbelow).

Preparation Example 2

A hard coating was formed on a TAC film in the same way as in Preparation Example 1 to prepare a TAC film with hard coating (abbreviated as HC-TAC hereinbelow). Next, 240 parts by weight of toluene dispersion containing 30% zinc oxide powders (trade name "ZN-300", manufactured by SUMITOMO OSAKACEMENT CO. LTD.), 28 parts by weight of trimethylolpropane triacrylate (abbreviated as TMPTA hereinbelow), 1 part by weight of "DAROCUR1116" (trade name, manufactured by E. MELCK CORPORATION, acetophenone compound) (abbreviated as "DAROCUR1116" hereinbelow) as a curing initiator, and 1900 parts by weight of toluene as a solvent were mixed together to prepare a coating liquid. Subsequently, the coating liquid was applied to the HC-TAC by dip coating method (at pull-up rate of 100 mm/min.). The applied coating liquid was cured by irradiating with ultraviolet ray by an ultraviolet irradiator at 1000 mJ/cm$^2$ to form a layer of a high refractivity material, thereby preparing a TAC film with a layer of the high refractivity material (abbreviated as HR-TAC-A hereinbelow).

Preparation Example 3

A TAC film with a layer of the high refractivity material (abbreviated as HR-TAC-B hereinbelow) was prepared in the same way as in Preparation Example 2 except that the dip coating method was carried out at the pull-out rate of 130 mm/min.

Examples 4-1 and 4-2

Product A synthesized in Example 1-1 and tetramethylolmethane tetraacrylate (abbreviated as TMMTA hereinbelow) were mixed at the mixing ratio set forth in Table 1 to prepare monomer compositions. Each of the monomer compositions was mixed with 1900 parts by weight of toluene to prepare two kinds of coating liquids. Then, each of the coating liquids was applied to HC-PET prepared in Preparation Example 1 by a dip coating method (at pull-up rate of 90 mm/min.). The applied coating liquids were irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied monomer compositions, thereby preparing reflection reducing PET films with a layer of the low refractivity material. For evaluation, the films thus obtained were subjected to the measurements of (a) spectral reflectance, (b) abrasion resistance, and (c) adhesion, and the coating liquids thus obtained were subjected to the measurement of (e) refractive index of the low refractivity material, each specified below.

(a) Spectral Reflectance

Figure 2:
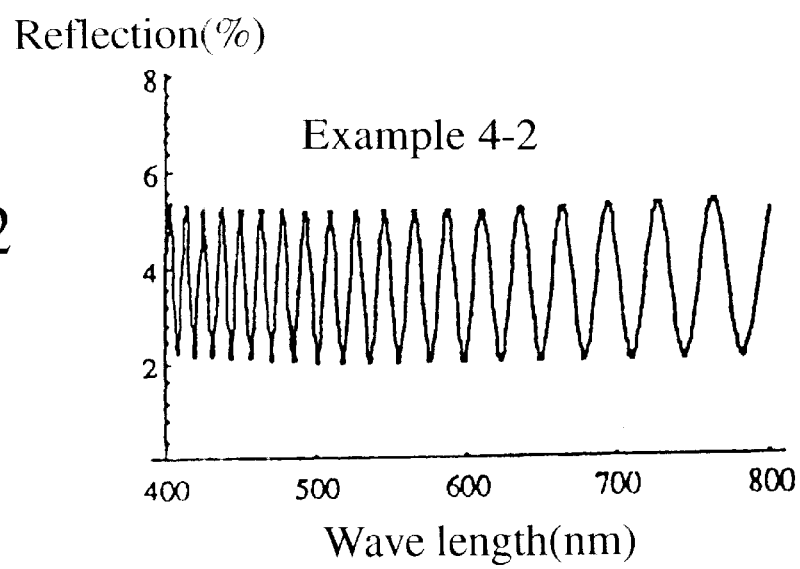
FIG. 2 is a graph showing the results of the measurements of the spectral reflectance in Example 4-2.

The spectral reflectance of the film was measured by an UV Spectrophotometer equipped with 5 degree specular reflectivity measuring attachment (manufactured by JAPAN SPECTROSCOPIC CO., LTD., trade name "U-best 35"). The measurement was effected on the coated surface, and the opposite surface of the film was roughened with a sandpaper for inhibiting reflection on the opposite surface. The results are shown in FIGS. 1 and 2. The minimum reflectance of each film is shown in Table1.

(b) Abrasion Resistance

The scratch resistance against #0000 steel wool was measured, and evaluated according to the evaluation standard below. The results are shown in Table 1.

A: No abrasion by vigorous rubbing
B: Slight abrasion by vigorous rubbing
C: Slight abrasion by soft rubbing
D: Remarkable abrasion by soft rubbing (c) Adhesion Cross cut test was conducted in accordance with JIS K 5400. The results are shown in Table 1.

(d) Refractive index of the low refractivity material

The coating liquid was applied on a glass plate so that the dry thickness of the resulting coating film was 500 μm, and cured by irradiating with electron beam of the absorbed dose of 5 Mrad by an electron beam irradiator at the accelerating voltage of 175 kV and the beam current of 5 mA. The film thus obtained was peeled off of the glass plate, and the refractive index of the film was measured using Abbe's refractometer (manufactured by ATAGO CO., LTD.). The results are shown in Table 1.

Examples 4-3 and 4-4

Figure 3:
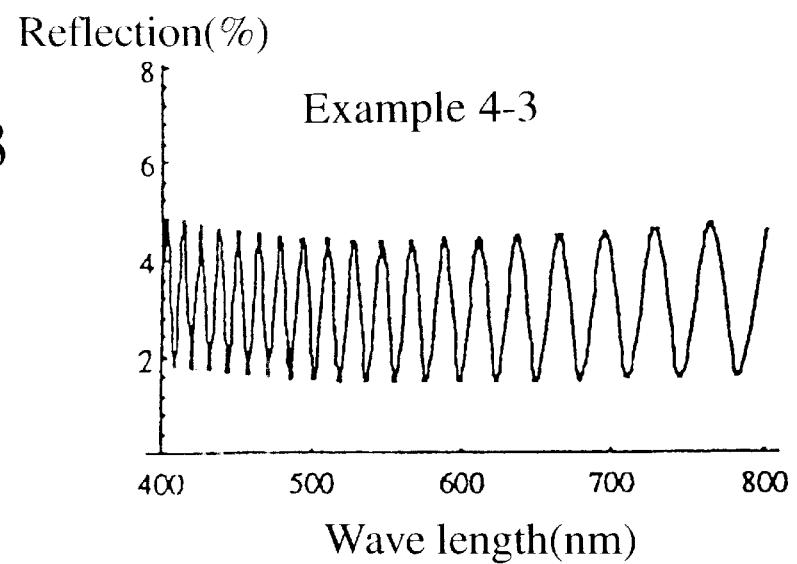
FIG. 3 is a graph showing the results of the measurements of the spectral reflectance in Example 4-3.
Figure 4:
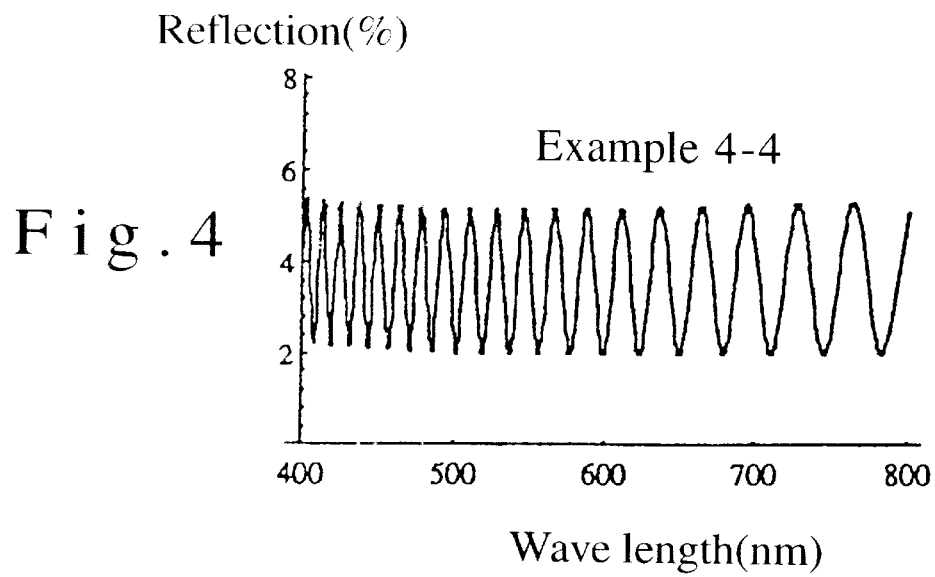
FIG. 4 is a graph showing the results of the measurements of the spectral reflectance in Example 4-4.

Product B synthesized in Example 1-2, 2,2,3,3,4,4,5,5,6,6,7,7,8,8,9,9,9-heptadecafluorononylethylene glycol diacrylate (abbreviated as F$_{17}$EDA hereinbelow), and TMMTA were mixed together at the mixing ratio set forth in Table 1 to prepare monomer compositions. Each of the monomer compositions was mixed with 1900 parts by weight of toluene as a solvent to prepare two kinds of coating liquids. Then, each of the coating liquids was applied to HC-PET prepared in Preparation Example 1 by a dip coating method (at pull-up rate of 90 mm/min.). The applied coating liquids were irradiated with electron beam of the absorbed dose of 15 Mrad by an electron beam irradiator (manufactured by IWASAKI ELECTRIC CO,. LTD.) at the accelerating voltage of 125 kV and the beam current of 35 mA to cure the appliedmonomer compositions, thereby preparing reflection reducing PET films with a layer of the low refractivity material. The coating liquids and the reflection reducing films thus obtained were subjected to the same evaluation tests as in Examples 4-1 and 4-2. The results are shown in FIGS. 3 and 4 and Table 1.

Examples 4-5 and 4-6

Figure 5:
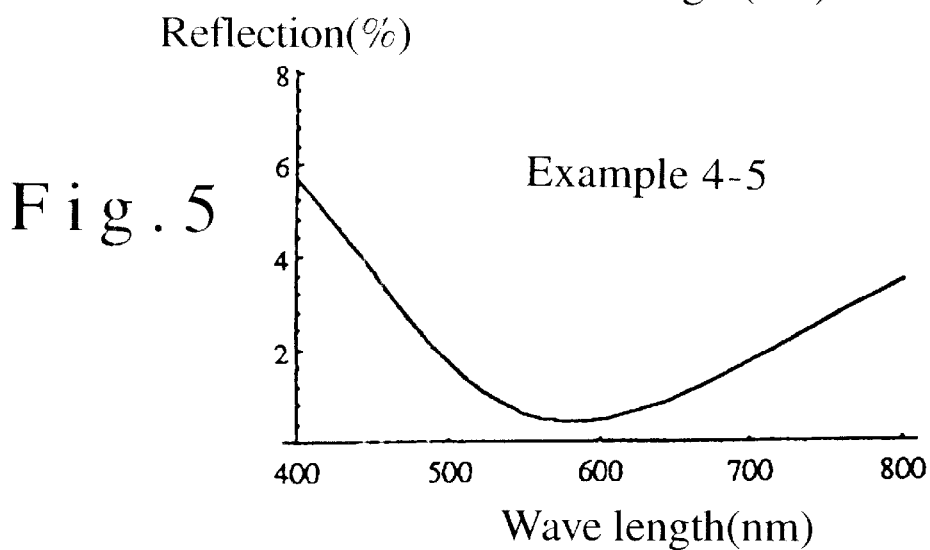
FIG. 5 is a graph showing the results of the measurements of the spectral reflectance in Example 4-5.
Figure 6:
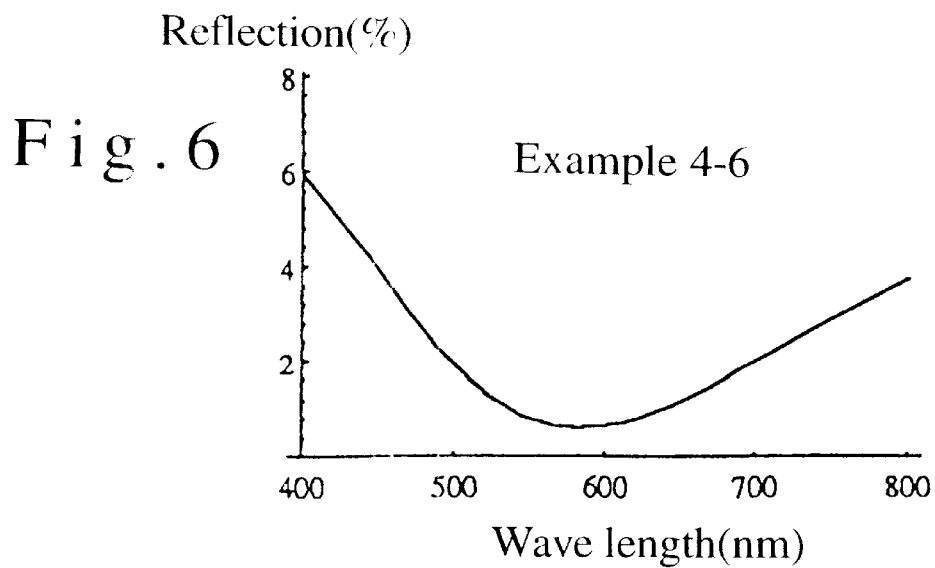
FIG. 6 is a graph showing the results of the measurements of the spectral reflectance in Example 4-6.

Product A synthesized in Example 1-1, product G synthesized in Example 3-1, "XBA-ST SILICA GEL" (trade name, manufactured by NISSAN CHEMICAL INDUSTRIES CO., LTD., colloidal silica 30%: xylene 45%:

n-butanol 25%), and DAROCUR1116 were mixed together at the mixing ratio set forth in Table 1 to prepare monomer compositions. Each of the monomer compositions was mixed with 1900 parts by weight of toluene to prepare two kinds of coating liquids. Then, each of the coating liquids was applied to HR-TAC-A prepared in Preparation Example 2 by a dip coating method (at pull-up rate of 90 mm/min.). The applied coating liquids were irradiated three times with ultraviolet ray by an ultraviolet irradiator at 1000 mJ/cm$^2$ to cure the applied monomer compositions, thereby preparing reflection reducing TAC films with laminated layers of the low refractivity material and the high refractivity material. The coating liquids and the reflection reducing films thus obtained were subjected to the same evaluation tests as in Examples 4-1 and 4-2. The results are shown in FIGS. 5 and 6 and Table 1.

Examples 4-7 and 4-8

Figure 7:
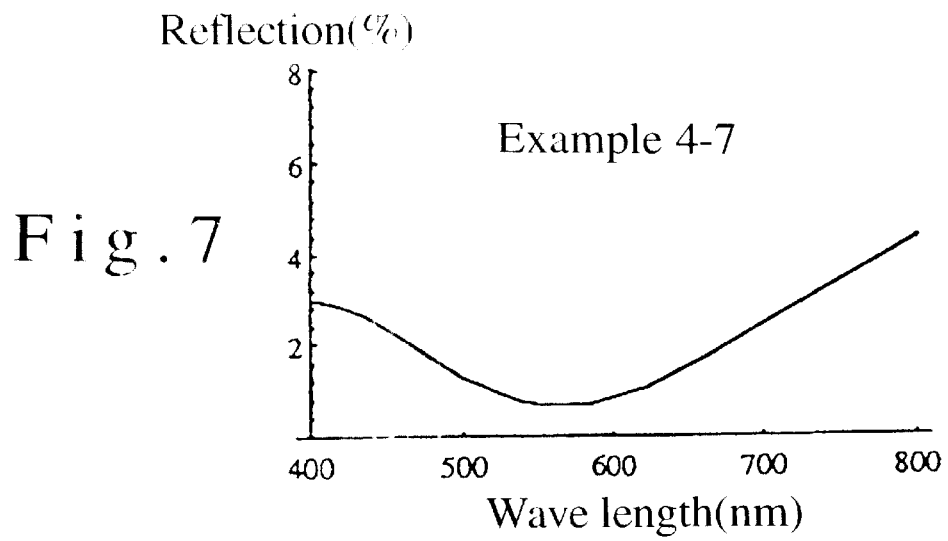
FIG. 7 is a graph showing the results of the measurements of the spectral reflectance in Example 4-7.
Figure 8:
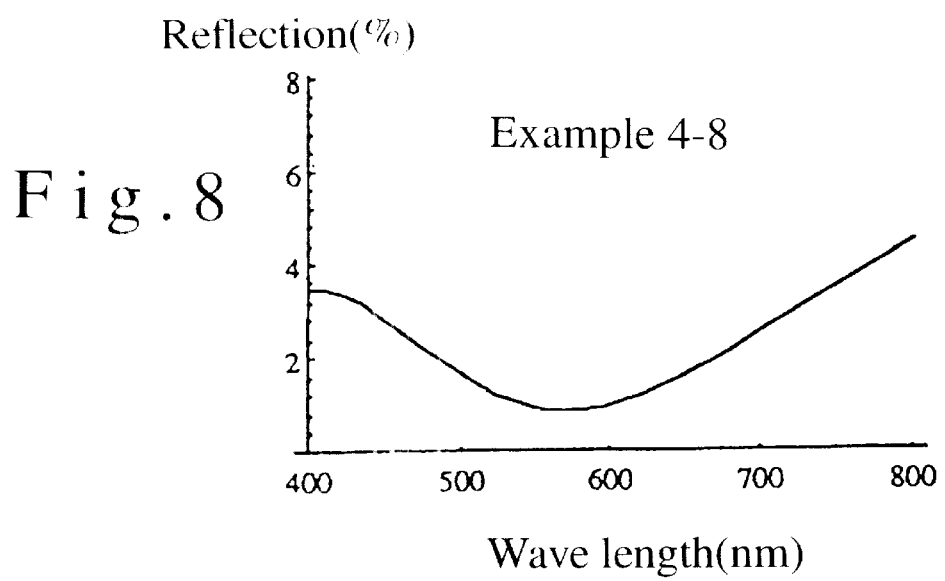
FIG. 8 is a graph showing the results of the measurements of the spectral reflectance in Example 4-8.

Reflection reducing TAC films with laminated layers of the low refractivity material and the high refractivity material were prepared in the same way as in Examples 4-5 and 4-6 except that HR-TAC-A prepared in Preparation Example 2 was replaced by HR-TAC-B prepared in Preparation Example 3. The dip coating method was performed at the pull-up rate of 70 mm/min. The coating liquids and the reflection reducing films thus obtained were subjected to the same evaluation tests as in Examples 4-1 and 4-2. The results are shown in FIGS. 7 and 8 and Table 1.

Comparative Examples 1 and 2

Figure 9:
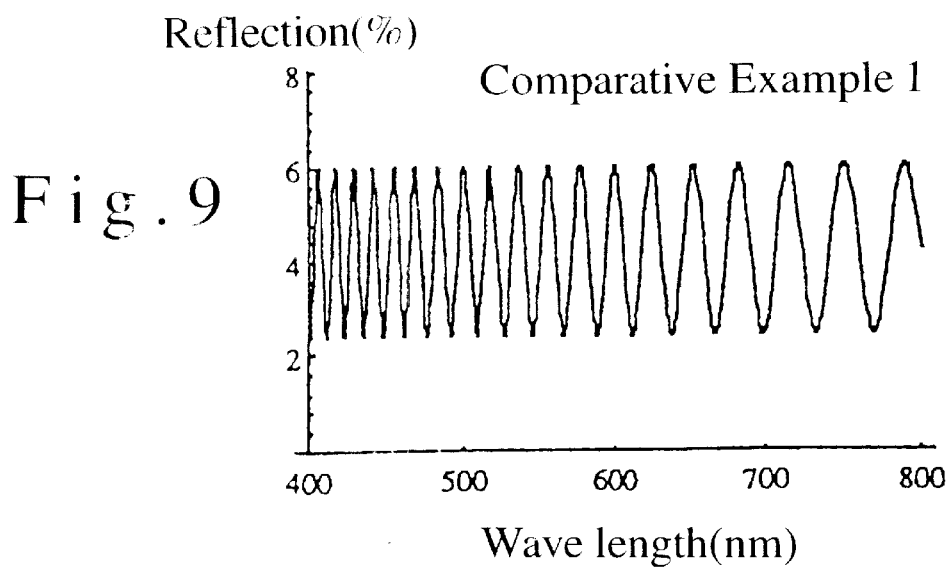
FIG. 9 is a graph showing the results of the measurements of the spectral reflectance in Comparative Example 1.
Figure 10:
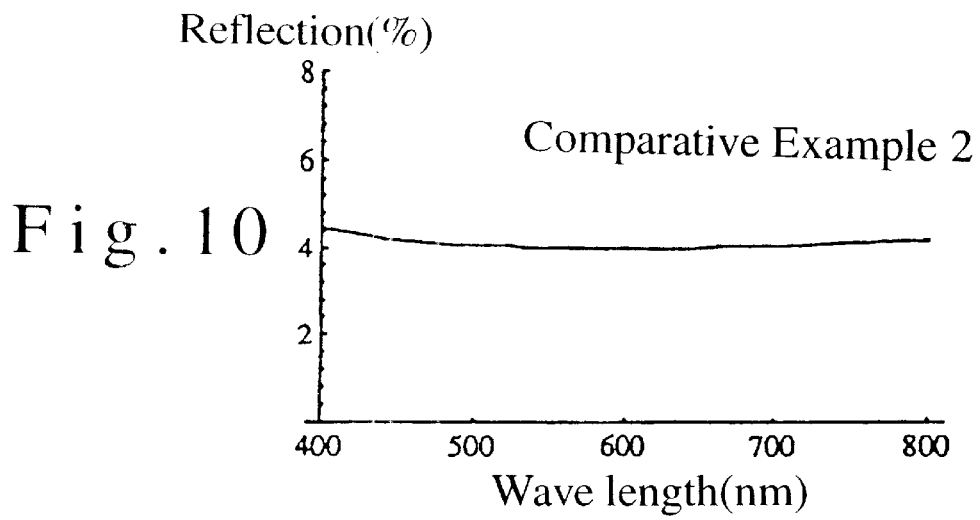
FIG. 10 is a graph showing the results of the measurements of the spectral reflectance in Comparative Example 2.

The spectral reflectance, the minimum reflectance, and the abrasion resistance of HC-PET and HC-TAC prepared in Preparation Examples 1 and 2, respectively, were measured in the same way as in Examples 4-1 and 4-2. The results are shown in FIGS. 9 and 10 and Table 1.

Comparative Example 3

Figure 11:
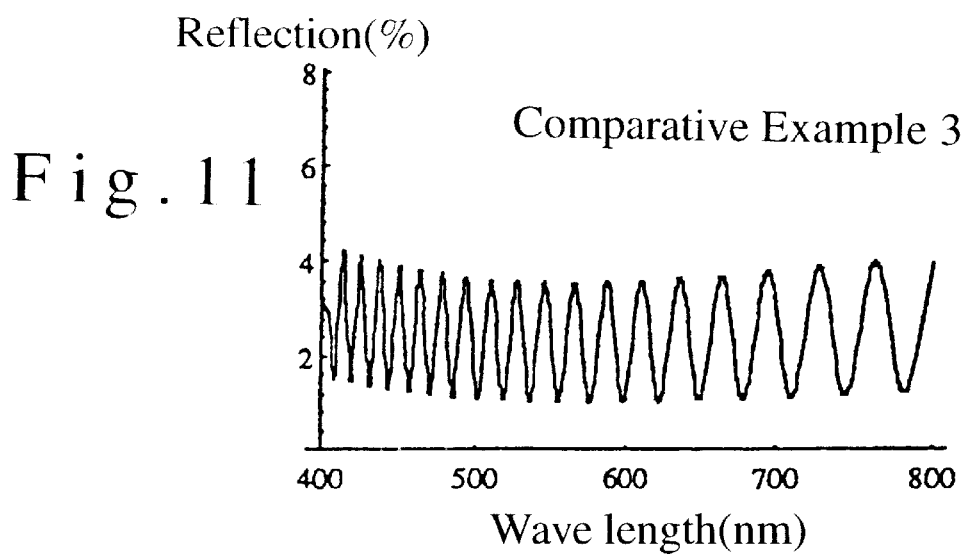
FIG. 11 is a graph showing the results of the measurements of the spectral reflectance in Comparative Example 3.

$F_{17}$EDA and TMMTA were mixed at the mixing ratio set forth in Table 1, and further mixed with 1900 parts by weight of toluene as a solvent to prepare a coating liquid. Then the coating liquid thus obtained was applied to HC-PET prepared in Preparation Example 1 by dip coating method (at the pull-up rate of 90 mm/min.). The applied coating liquid was irradiated with electron beam of the absorbed dose of 15 Mrad by an electron beam irradiator (manufactured by IWASAKI ELECTRIC CO., LTD.) at the accelerating voltage of 125 kV and the beam current of 35 mA to cure the applied coating liquid, thereby preparing a reflection reducing PET film with a layer of the low refractivity material. The coating liquid and the reflection reducing film thus obtained were subjected to the same evaluation tests as in Examples 4-1 and 4-2. The results are shown in FIG. 11 and Table 1.

Comparative Example 4

Heptadecafluorodecyl acrylate (abbreviated as $F_{17}$A hereinbelow) and TMMTA were mixed at the mixing ratio of 70:30, 50:50, and 30:70, but were not mutually dissolved and exhibited turbid appearance.

In Tables 1 to 3, XBA-ST denotes "XBA-ST SILICA SOL" (trade name) manufactured by NISSAN CHEMICAL INDUSTRIES CO., LTD. consistingofcolloidal silica 30%: xylene45%: n-butanol 25%, and D.1116 denotes "DAROCUR1116" (trade name) manufactured by E. MELCK CORPORATION, 1-(4-isopropylphenyl)-2-hydroxy-2-methylpropane-1-one.

TABLE 1

| | | Fluorine-containing bifunctional monomer containing OH | | Fluorine-containing monomer | | Poly-functional monomer | In-organic powders | Curing initiator | | | | |
|---|---|---|---|---|---|---|---|---|---|---|---|---|
| | Substrate film | Product A parts by weight | Product B parts by weight | tetra-functional Product G parts by weight | bi-functional $F_{17}$EDA parts by weight | TMMTA parts by weight | XBA-ST parts by weight | D.1116 parts by weight | Minimum reflection | Adhesion | Scratch resistance | Refractive index |
| Ex. 4-1 | HC-PET | 80 | — | — | — | 20 | — | — | 1.5 | 100/100 | C | 1.448 |
| Ex. 4-2 | HC-PET | 40 | — | — | — | 60 | — | — | 2.0 | 100/100 | B | 1.477 |
| Ex. 4-3 | HC-PET | — | 40 | — | 40 | 20 | — | — | 1.5 | 100/100 | C | 1.445 |
| Ex. 4-4 | HC-PET | — | 60 | — | — | 40 | — | — | 2.0 | 100/100 | B | 1.476 |
| Ex. 4-5 | HR-TAC-A | 50 | — | 35 | — | — | 50 | 1 | 0.5 | 100/100 | B | 1.444 |
| Ex. 4-6 | HR-TAC-A | 10 | — | 45 | — | — | 150 | 1 | 0.6 | 100/100 | A | 1.470 |
| Ex. 4-7 | HR-TAC-B | 50 | — | 35 | — | — | 50 | 1 | 0.7 | 100/100 | B | 1.443 |
| Ex. 4-8 | HR-TAC-B | 10 | — | 45 | — | — | 150 | 1 | 0.9 | 100/100 | A | 1.470 |
| Comp. Ex. 1 | HC-PET | — | — | — | — | — | — | — | 2.4 | | A | |
| Comp. Ex. 2 | HC-TAC | — | — | — | — | — | — | — | 4.0 | | A | |
| Comp. Ex. 3 | HC-PET | — | — | — | 70 | 30 | — | — | 1.1 | 30/100 | D | 1.421 |

Examples 5-1 and 5-2

Figure 12:
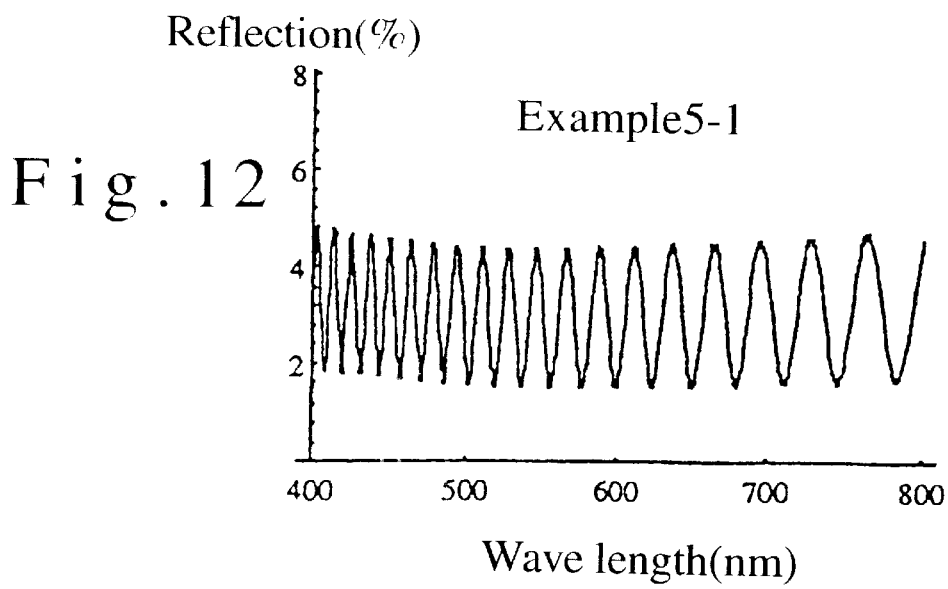
FIG. 12 is a graph showing the results of the measurements of the spectral reflectance in Example 5-1.
Figure 13:
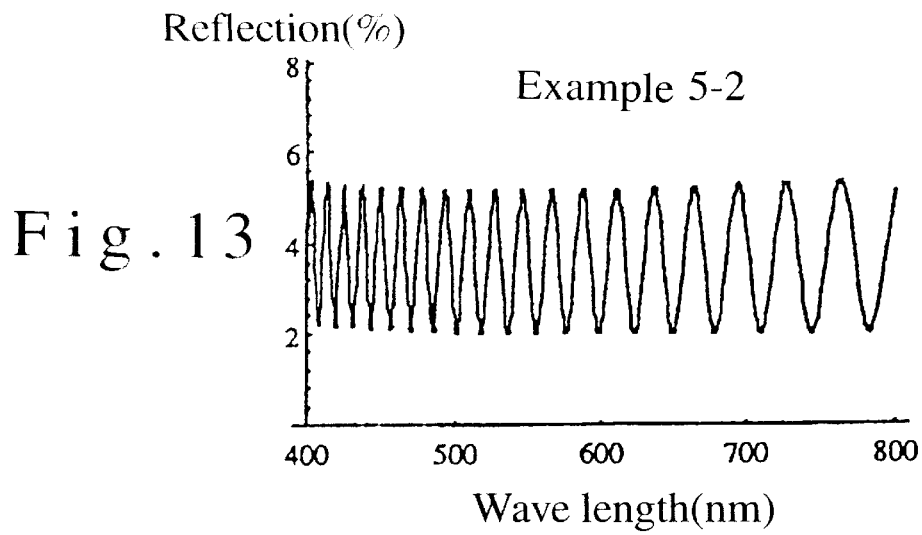
FIG. 13 is a graph showing the results of the measurements of the spectral reflectance in Example 5-2.

Product D synthesized in Example 2-1 and TMMTA were mixed at the mixing ratio set forth in Table 2 to prepare monomer compositions. Each of the monomer compositions was mixed with 1900 parts by weight of toluene to prepare two kinds of coating liquids. Then, reflection reducing PET films with a layer of the low refractivity material were prepared, and subjected to evaluation tests in the same way as in Examples 4-1 and 4-2. The results are shown in FIGS. 12 and 13 and Table 2.

Examples 5-3 and 5-4

Product E synthesized in Example 2-2, $F_{17}$EDA, and TMMTA were mixed together at the mixing ratio set forth in Table 2 to prepare monomer compositions. Each of the monomer compositions was mixed with 1900 parts by weight oftoluenetopreparetwo kinds of coating liquids.

Figure 14:
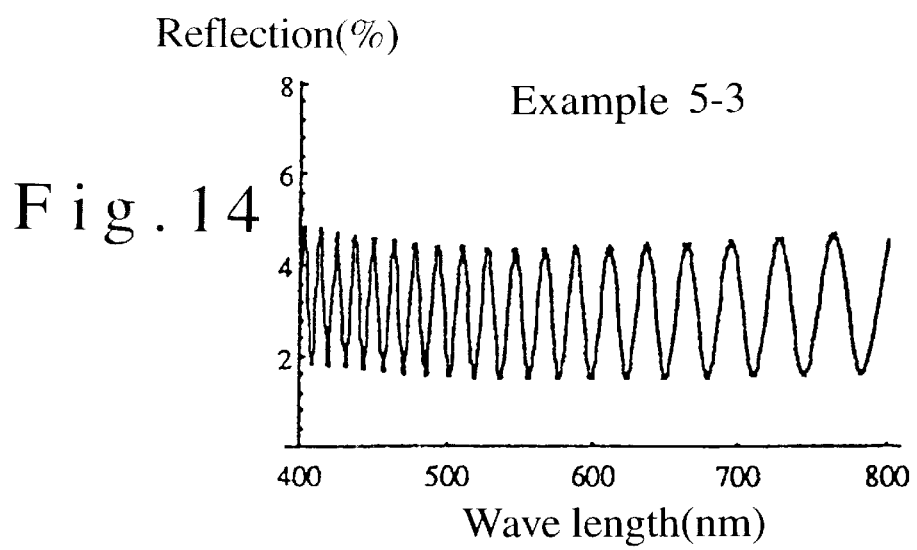
FIG. 14 is a graph showing the results of the measurements of the spectral reflectance in Example 5-3.
Figure 15:
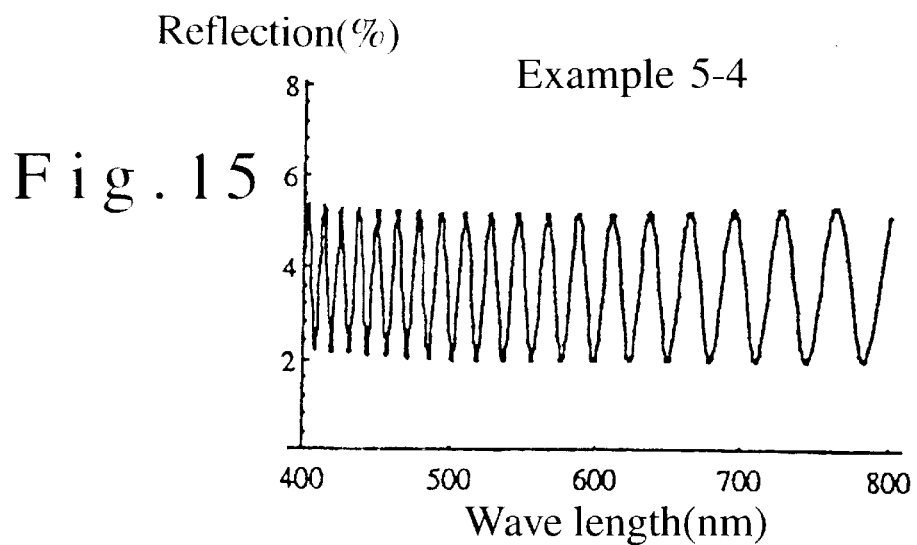
FIG. 15 is a graph showing the results of the measurements of the spectral reflectance in Example 5-4.

Then, reflection reducing PET films with a layer of the low refractivity material were prepared, and subjected to the evaluation tests in the same way as in Examples 4-3 and 4-4. The results are shown in FIGS. 14 and 15 and Table 2.

Examples 5-5 and 5-6

Figure 16:
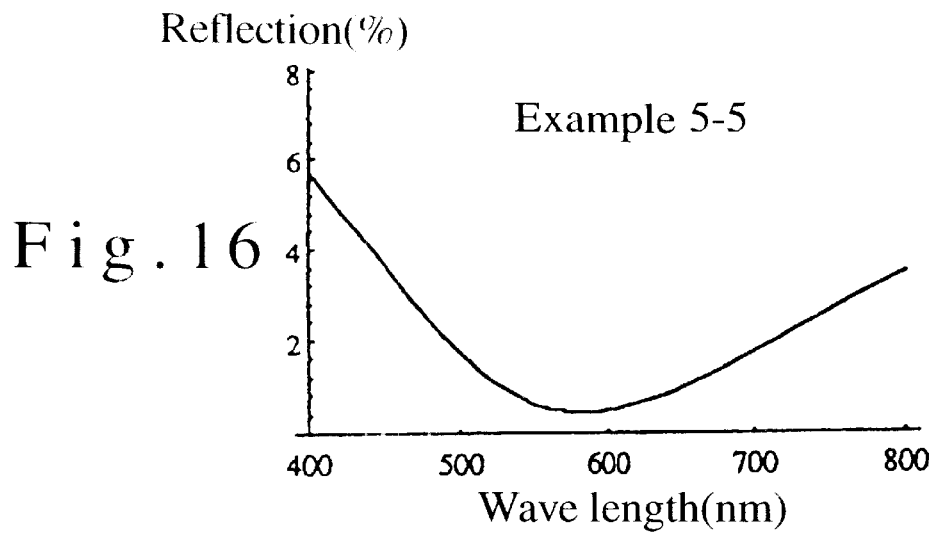
FIG. 16 is a graph showing the results of the measurements of the spectral reflectance in Example 5-5.
Figure 17:
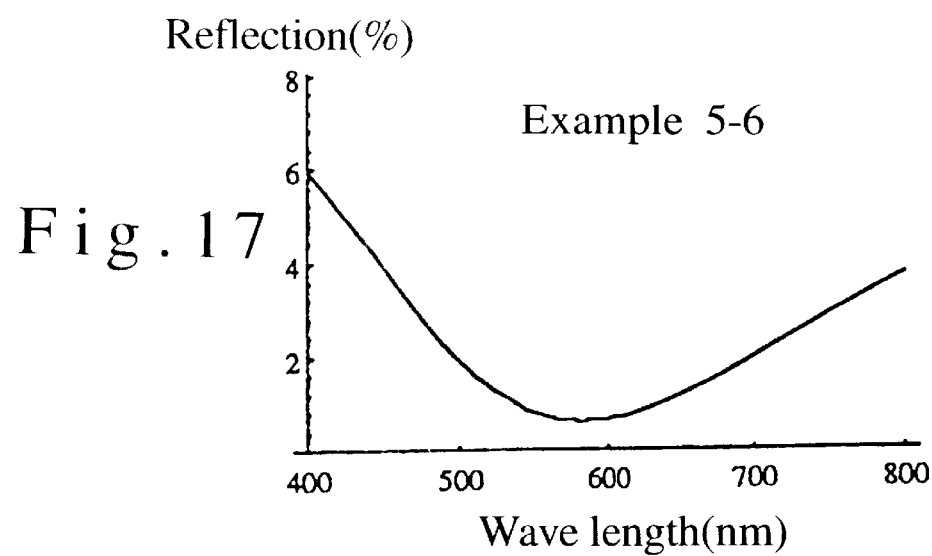
FIG. 17 is a graph showing the results of the measurements of the spectral reflectance in Example 5-6.

Product D synthesized in Example 2-1, product G synthesized in Example 3-1, "XBA-ST SILICA GEL" (trade name, manufactured by NISSAN CHEMICAL INDUSTRIES CO., LTD., colloidal silica 30%: xylene 45%: n-butanol 25% ) and DAROCUR1116 were mixed together at the mixing ratio set forth in Table 2 to prepare monomer compositions. Each of the compositions was mixed with 1900 parts by weight of toluene as a solvent to prepare two kinds of coating liquids. Then, reflection reducing TAC films with laminated layers of the low refractivity material and the high refractivity material, and subjected to evaluation tests in the same way as in Examples 4-5 and 4-6. The results are shown in FIGS. 16 and 17 and Table 2.

Examples 5-7 and 5-8

Figure 18:
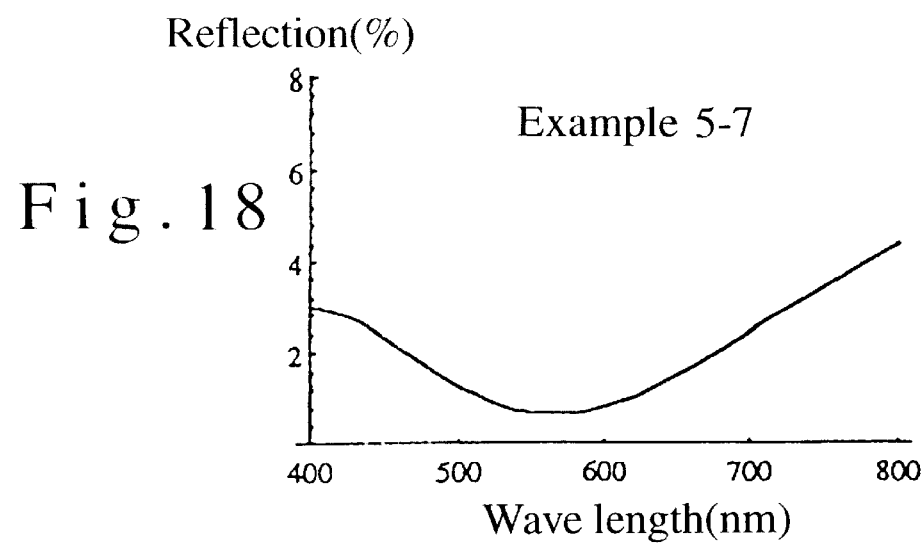
FIG. 18 is a graph showing the results of the measurements of the spectral reflectance in Example 5-7.
Figure 19:
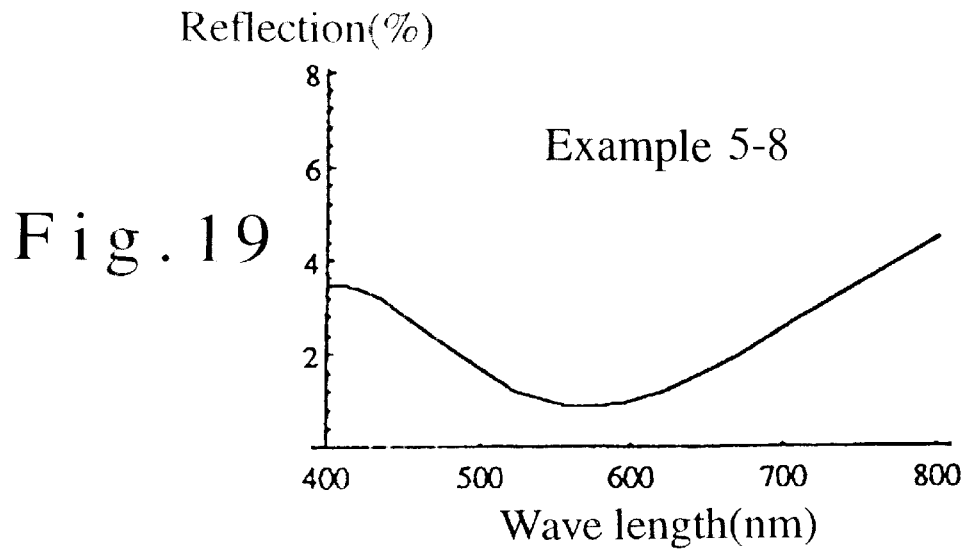
FIG. 19 is a graph showing the results of the measurements of the spectral reflectance in Example 5-8.
Figure 22:
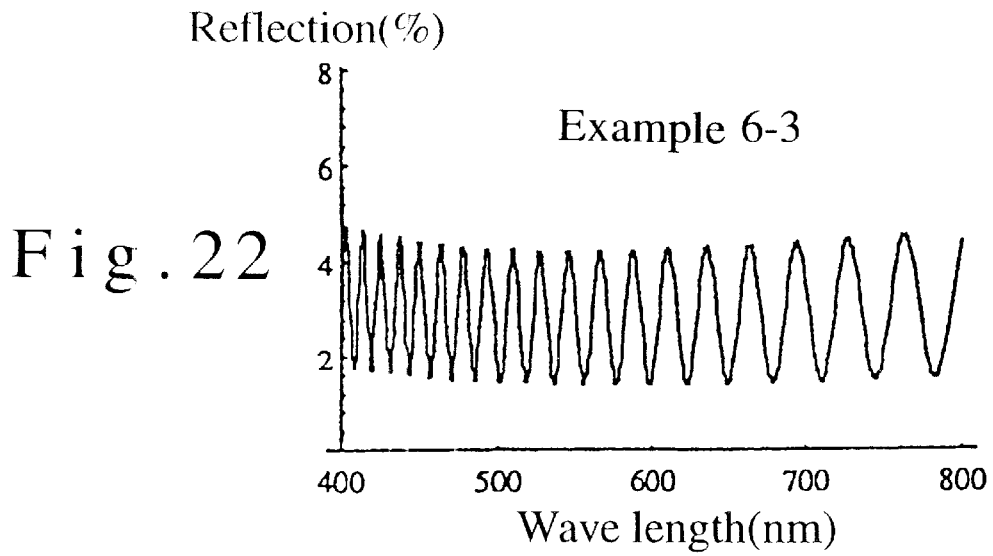
FIG. 22 is a graph showing the results of the measurements of the spectral reflectance in Example 6-3.
Figure 23:
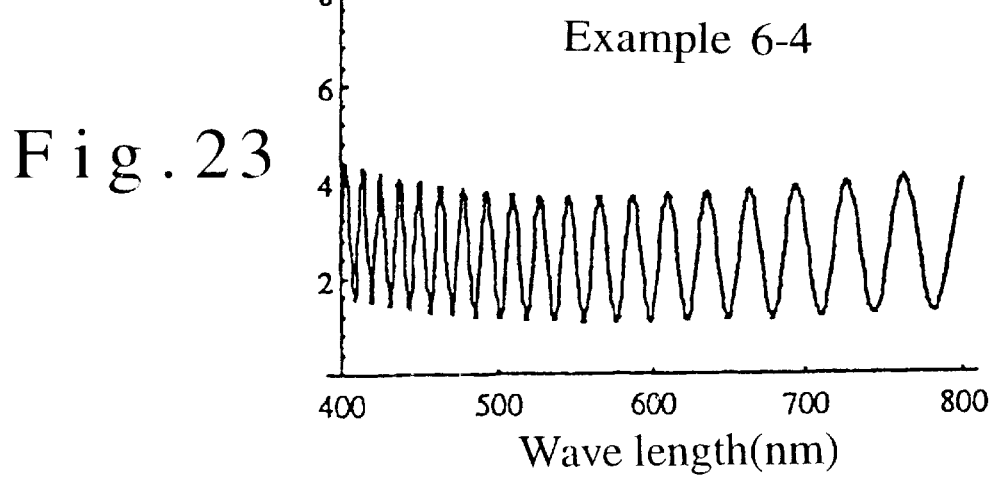
FIG. 23 is a graph showing the results of the measurements of the spectral reflectance in Example 6-4.

Reflection reducing TAC films with laminated layers of the low refractivity material and the high refractivity material were prepared in the same way as in Examples 5-5 and 5-6 except that HR-TAC-A prepared in Preparation Example 2 was replaced by HR-TAC-B prepared in Preparation Example 3. The coating liquids and the reflection reducing films thus obtained were subjected to the evaluation tests. The results are shown in FIGS. 18 and 19 and Table 2.

prepare monomer compositions. Each of the compositions was mixed with 1900 parts by weight of toluene to prepare two kinds of coating liquids. Then, reflection reducing PET films with a layer of the low refractivity material were prepared in the same way as in Examples 4-3 and 4-4, and subjected to the evaluation tests in the same way as in Examples 6-1 and 6-2. The results are shown in FIGS. 22 and 23 and Table 3.

Examples 6-5 and 6-6

Figure 24:
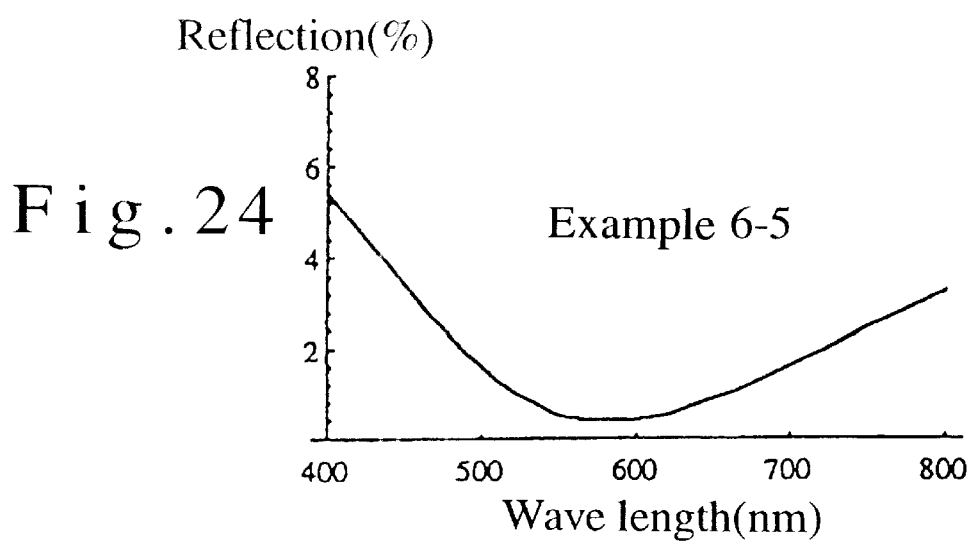
FIG. 24 is a graph showing the results of the measurements of the spectral reflectance in Example 6-5.
Figure 25:
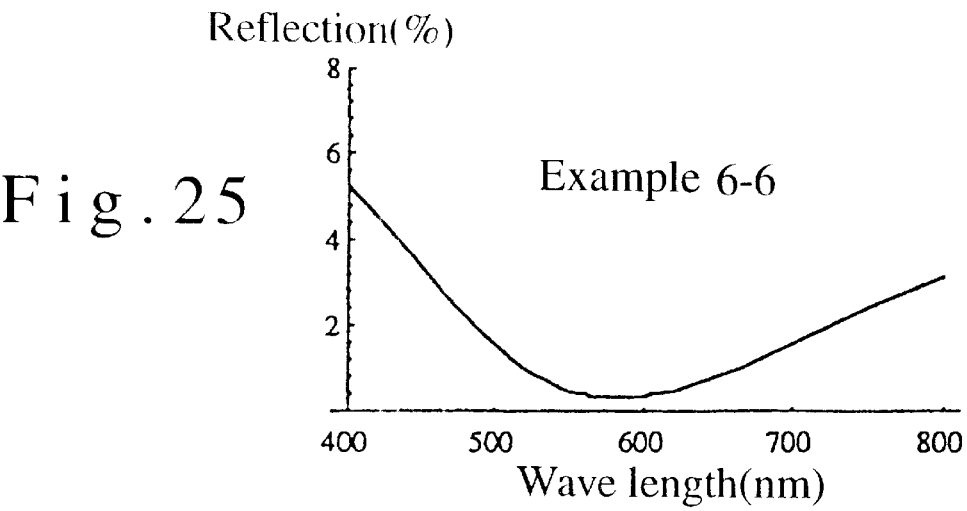
FIG. 25 is a graph showing the results of the measurements of the spectral reflectance in Example 6-6.

Product G synthesized in Example 3-1, $F_{17}EDA$, and DAROCUR1116 were mixed together at the mixing ratio set forth in Table 3 to prepare monomer compositions. Each of the compositions was mixed with 1900 parts by weight of toluene as a solvent to prepare two kinds of coating liquids. Then, reflection reducing TAC films with laminated layers of the low refractivity material and the high refractivity material were prepared in the same way as in Examples 4-5 and 4-6, and subjected to the evaluation tests in the same way as in Examples 6-1 and 6-2. The results are shown in FIGS. 24 and 25 and Table 3.

Examples 6-7 and 6-8

In accordance with the method of Examples 6-5 and 6-6, reflection reducing TAC films with laminated layers of the low refractivity material and the high refractivity material were prepared except that the HR-TAC-A prepared in Preparation Example 2 was replaced by HR-TAC-B prepared in Preparation Example 3. The coating liquids and the reflec-

TABLE 2

| | | Fluorine-containing bifunctional monomer containing OH | | Fluorine-containing monomer | | Poly- | In- | | | | | |
|---|---|---|---|---|---|---|---|---|---|---|---|---|
| | Substrate film | Product D parts by weight | Product E parts by weight | tetra-functional Product G parts by weight | bi-functional $F_{17}EDA$ parts by weight | functional monomer TMMTA parts by weight | organic powders XBA-ST parts by weight | Curing initiator D.1116 parts by weight | Minimum reflection | Adhesion | Scratch resistance | Refractive index |
| Ex. 5-1 | HC-PET | 90 | — | — | — | 10 | — | — | 1.5 | 100/100 | C | 1.449 |
| Ex. 5-2 | HC-PET | 40 | — | — | — | 60 | — | — | 2.0 | 100/100 | B | 1.474 |
| Ex. 5-3 | HC-PET | — | 40 | — | 40 | 20 | — | — | 1.5 | 100/100 | C | 1.444 |
| Ex. 5-4 | HC-PET | — | 80 | — | — | 20 | — | — | 2.0 | 100/100 | B | 1.477 |
| Ex. 5-5 | HR-TAC-A | 55 | — | — | 15 | — | 100 | 1 | 0.5 | 100/100 | B | 1.445 |
| Ex. 5-6 | HR-TAC-A | 10 | — | 45 | — | — | 150 | 1 | 0.6 | 100/100 | A | 1.471 |
| Ex. 5-7 | HR-TAC-B | 50 | — | — | 15 | — | 100 | 1 | 0.7 | 100/100 | B | 1.445 |
| Ex. 5-8 | HR-TAC-B | 10 | — | 45 | — | — | 150 | 1 | 0.9 | 100/100 | A | 1.471 |

Examples 6-1 and 6-2

Figure 20:
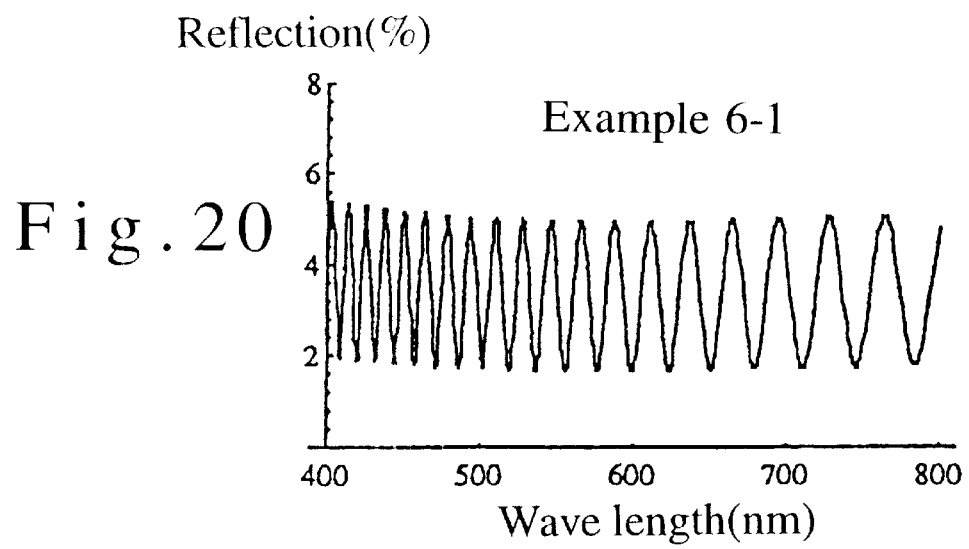
FIG. 20 is a graph showing the results of the measurements of the spectral reflectance in Example 6-1.
Figure 21:
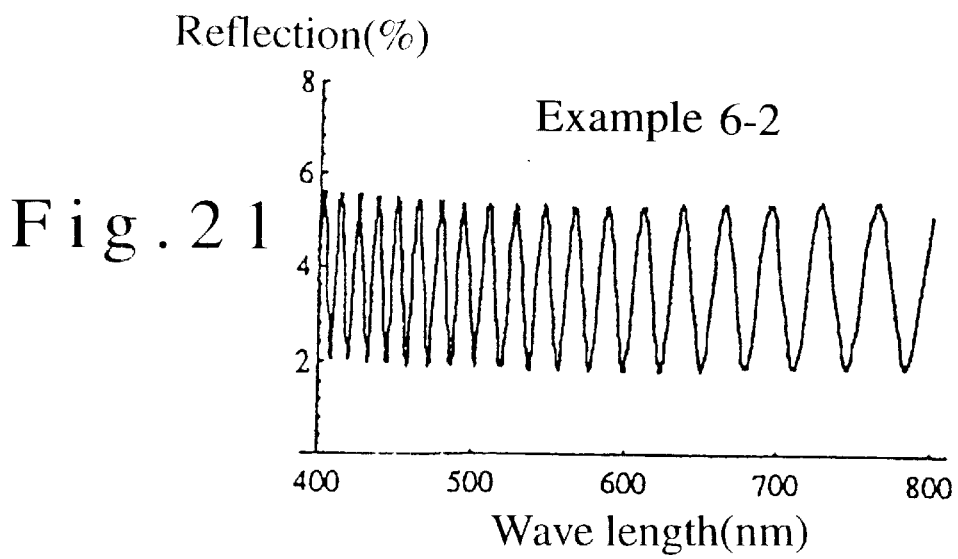
FIG. 21 is a graph showing the results of the measurements of the spectral reflectance in Example 6-2.

Product G synthesized in Example 3-1 and TMMTA were mixed together at the mixing ratio set forth in Table 3 to prepare monomer compositions. Each of the monomer compositions was mixed with 1900 parts by weight of toluene to prepare two kinds of coating liquids. Then, reflection reducing films with a layer of the low refractivity material were prepared in the same way as in Examples 4-1 and 4-2, and subjected to measurements of (a) the spectral reflection and (b) the abrasion resistance discussed above. The coating liquids were subjected to the measurement of (d) the refractive index discussed above. The results are shown in FIGS. 20 and 21 and Table 3.

Examples 6-3 and 6-4

Figure 26:
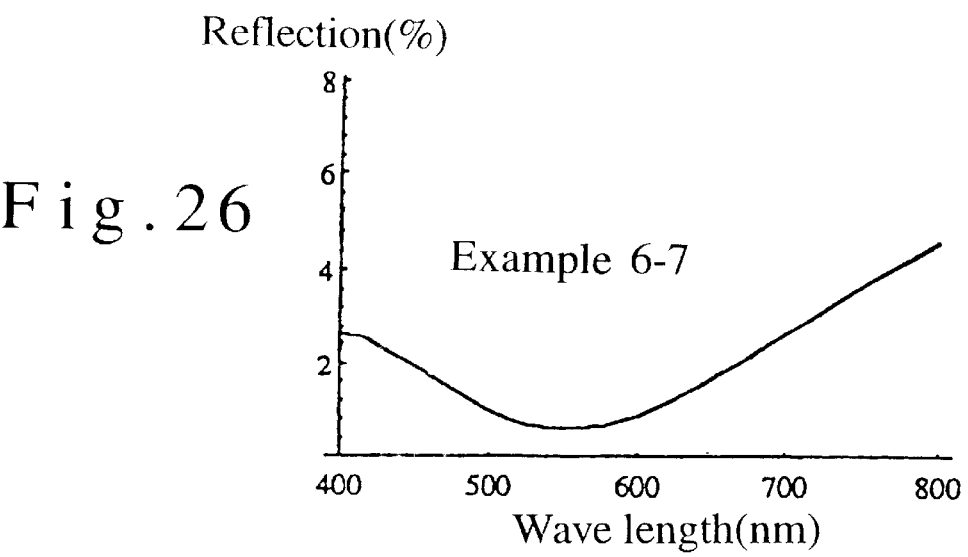
FIG. 26 is a graph showing the results of the measurements of the spectral reflectance in Example 6-7.
Figure 27:
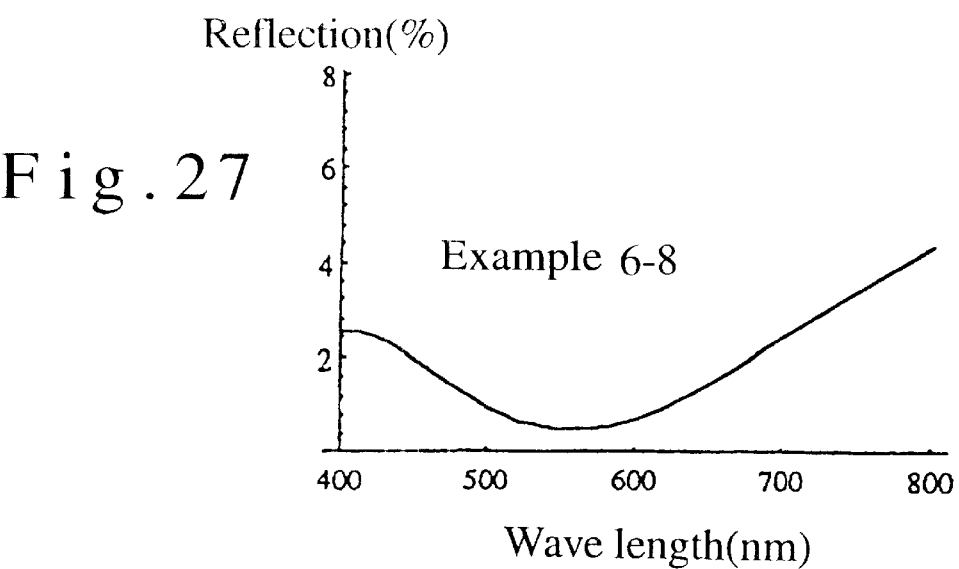
FIG. 27 is a graph showing the results of the measurements of the spectral reflectance in Example 6-8.

Product G synthesized in Example 3-1 and $F_{17}A$ were mixed together at the mixing ratio set forth in Table 3 to tion reducing films thus obtained were subjected to the same evaluation tests as in Examples 6-1 and 6-2. The results are shown in FIGS. 26 and 27 and Table 3.

Examples 6-9 and 6-10

Figure 28:
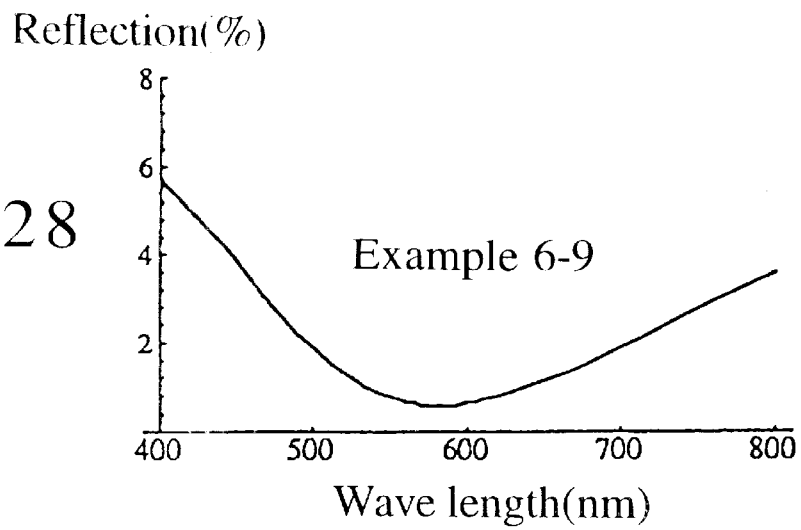
FIG. 28 is a graph showing the results of the measurements of the spectral reflectance in Example 6-9.
Figure 29:
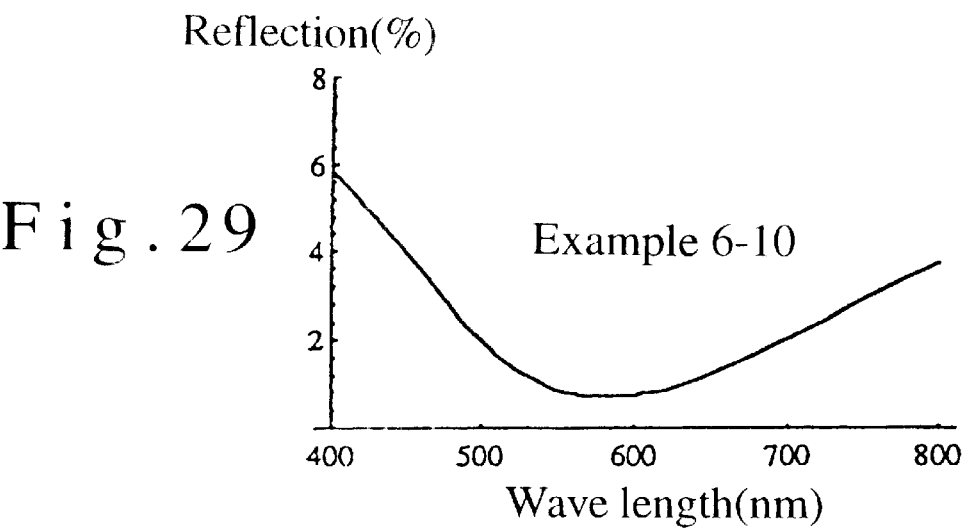
FIG. 29 is a graph showing the results of the measurements of the spectral reflectance in Example 6-10.
Figure 30:
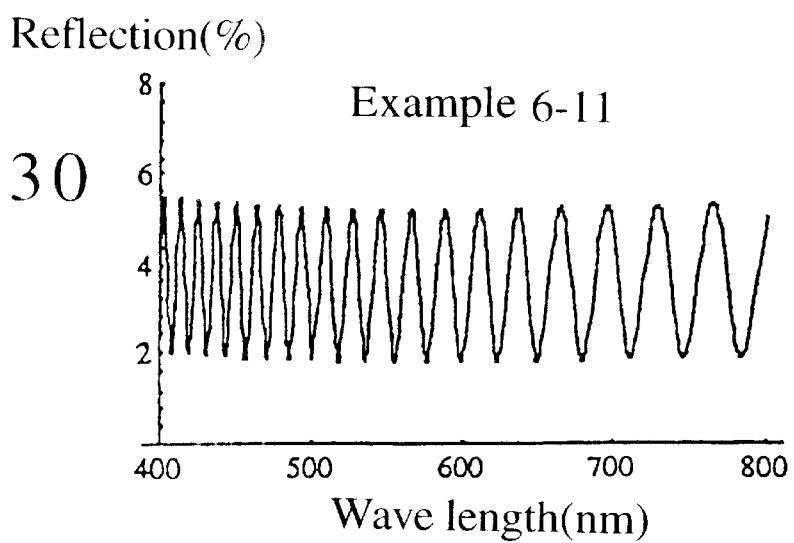
FIG. 30 is a graph showing the results of the measurements of the spectral reflectance in Example 6-11.
Figure 31:
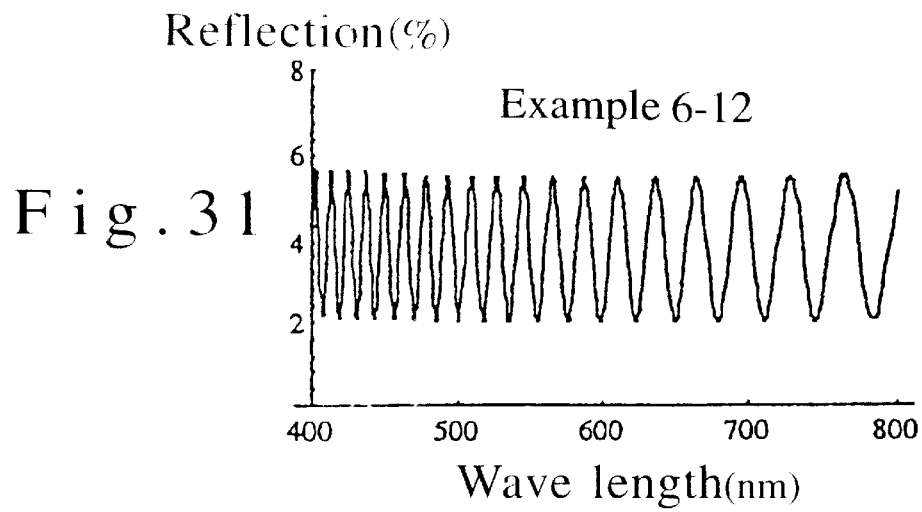
FIG. 31 is a graph showing the results of the measurements of the spectral reflectance in Example 6-12.
Figure 32:
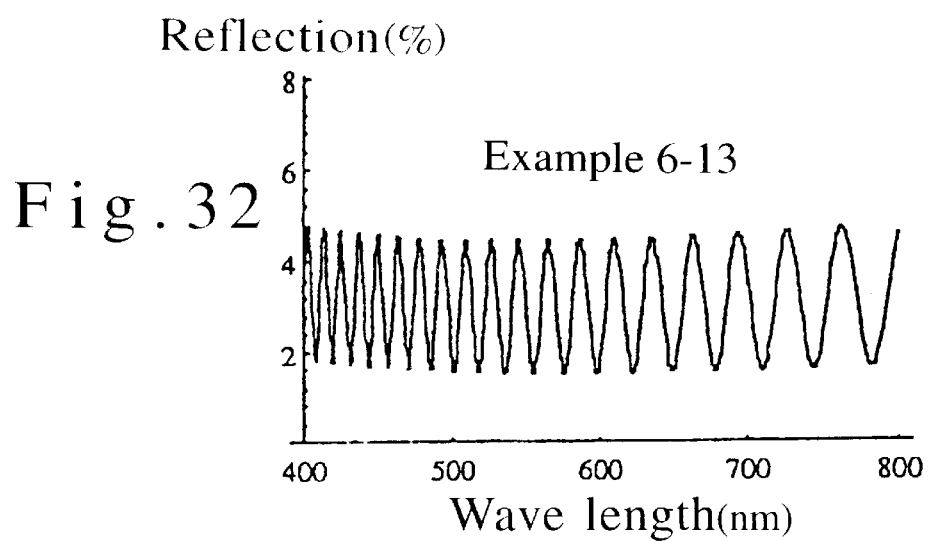
FIG. 32 is a graph showing the results of the measurements of the spectral reflectance in Example 6-13.
Figure 33:
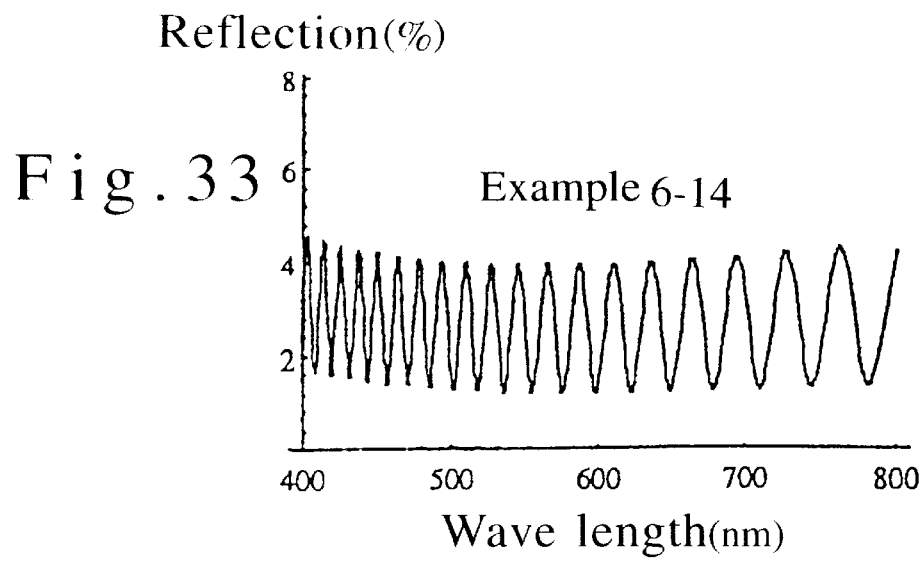
FIG. 33 is a graph showing the results of the measurements of the spectral reflectance in Example 6-14.

Product G synthesized in Example 3-1, TMPTA, "XBA-ST SILICA SOL" (trade name, manufactured by NISSAN CHEMICAL INDUSTRIES CO., LTD., colloidal silica 30%: xylene 45%: n-butanol 25% ), and DAROCURE1116 were mixed together at the mixing ratio set forth in Table 3 to prepare monomer compositions. Each of the compositions was mixed with 1900 parts by weight of toluene as a solvent to prepare two kinds of coating liquids. Then, each coating liquid was applied to HR-TAC-A prepared in Preparation Example 2 bydipcoatingmethod (at the pull-up rate of 90 mm/min.). The applied coating liquids were irradiated three times with ultraviolet ray by an ultraviolet irradiator at 1000 mJ/cm$^2$ to cure the coating liquid, thereby preparing reflection reducing TAC films with laminated layers of the low refractivity material and the high refractivity material. The coating liquids and the reflection reducing films thus obtained were subjected to the evaluation tests as in Examples 6-1 and 6-2. The results are shown in FIGS. 28 and 29 and Table 3.

Examples 6-11 to 6-14

Product H synthesized in Example 3-2, and $F_{17}A$, TMMTA or $F_{17}EDA$ were mixed together at the mixing ratio set forth in Table 3 to prepare monomer compositions. Each of the compositions was mixed with 1900 parts by weight of toluene as a solvent to prepare four kinds of coating liquids. Then, each coating liquid was applied to HC-PET prepared in Preparation Example 1 by dip coating method (at the pull-up rate of 90 mm/min.). The applied coating liquids were irradiated with electron beam of the absorbed dose of 15 Mrad by an electron beam irradiator at the accelerating voltage of 125 kV and beam current of 35 mA to cure the coating liquids, thereby preparing reflection reducing PET films with a layer of the low refractivity material. The coating liquids and the reflection reducing films thus obtained were subjected to the evaluation tests as in Examples 6-1 and 6-2. The results are shown in FIGS. 30 to 33 and Table 3.

Comparative Example 5

Figure 34:
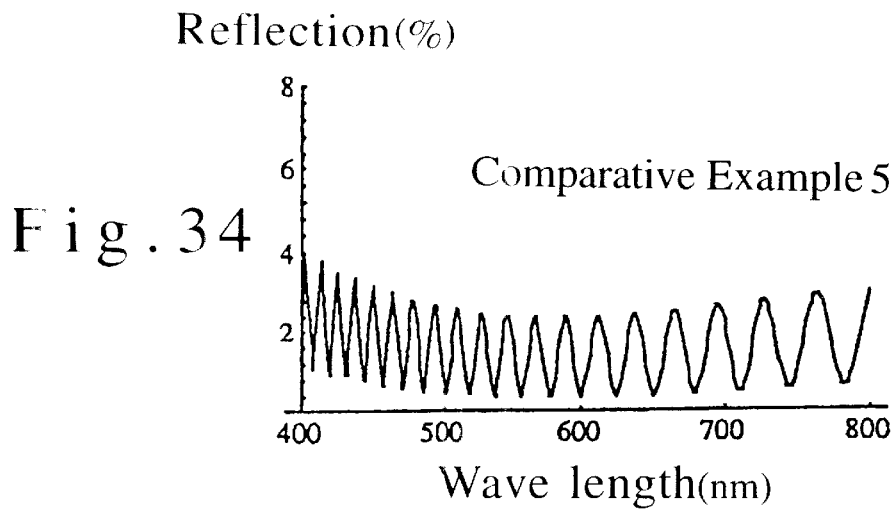
FIG. 34 is a graph showing the results of the measurements of the spectral reflectance in Comparative Example 5.

100 parts by weight of $F_{17}A$ and 1900 parts by weight of toluene as a solvent were mixed together to prepare a coating liquid. Then, a reflection reducing PET film was prepared in the same way as in Comparative Example 3. The coating liquid and the reflection reducing film thus obtained were subjected to the same evaluation tests as in Examples 6-1 and 6-2. The results are shown in FIG. 34 and Table 3.

Comparative Examples 6 and 7

Figure 35:
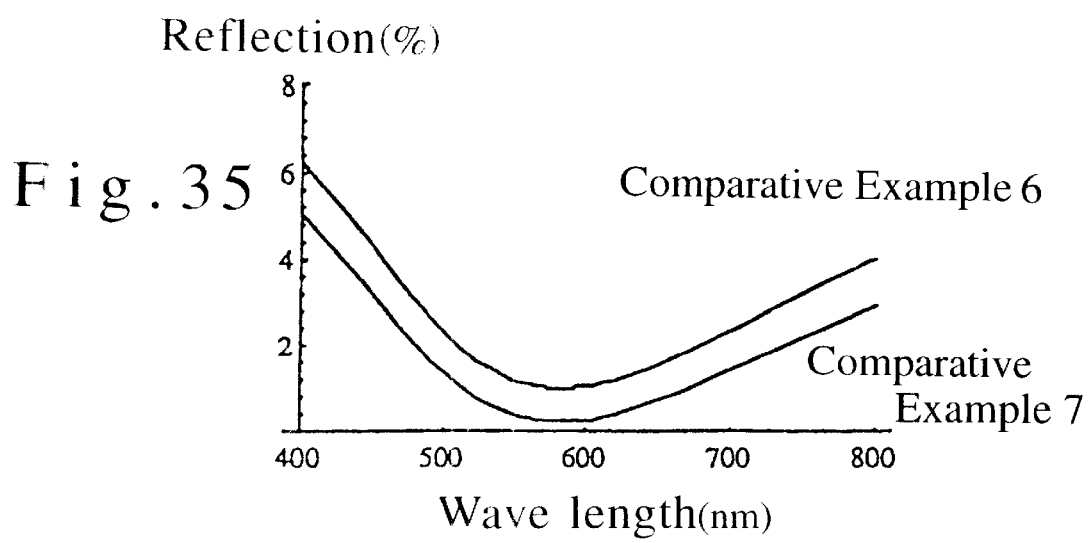
FIG. 35 is a graph showing the results of the measurements of the spectral reflectance in Comparative Examples 6 and 7.

$F_{17}EDA$ or TMMTA, and DAROCUR1116 were mixed together at the mixing ratio set forth in Table 3, and each of the resulting mixture was further mixed with 1900 parts by weight of toluene as a solvent to prepare two kinds of coating liquids. Each of the coating liquids was applied to HR-TAC-A prepared in Preparation Example 2 by dip coating method (at the pull-up rate of 90mm/min.). Then, the applied coating liquids were irradiated three times with ultraviolet ray by an ultraviolet irradiator at 1000 mJ/cm$^2$ to cure the coating liquids, thereby preparing reflection reducing films with a layer of the low refractivity material. The coating liquids and the reflection reducing films thus obtained were subjected to the same evaluation tests as in Examples 6-1 and 6-2. The results are shown in FIG. 35 and table 3.

TABLE 3

| | | Fluorine-containing tetrafunctional monomer | | Fluorine-containing monomer | | Polyfunctional monomer | | Inorganic powders | Curing initiator | | | |
| --- | --- | --- | --- | --- | --- | --- | --- | --- | --- | --- | --- | --- |
| | | | | mono-functional | bi-functional | | | | | | | |
| | Substrate film | Product G parts by weight | Product H parts by weight | $F_{17}A$ parts by weight | $F_{17}EDA$ parts by weight | TMMTA parts by weight | TMPTA parts by weight | XBA-ST parts by weight | D.1116 parts by weight | Minimum reflection | Scratch resistance | Refractive index |
| Ex. 6-1 | HC-PET | 70 | — | — | — | 30 | — | — | — | 1.7 | B | 1.462 |
| Ex. 6-2 | HC-PET | 50 | — | — | — | 5o | — | — | — | 1.9 | A | 1.475 |
| Ex. 6-3 | HC-PET | 90 | — | 10 | — | — | — | — | — | 1.4 | C | 1.440 |
| Ex. 6-4 | HC-PET | 70 | — | 30 | — | — | — | — | — | 1.i | C | 1.419 |
| Ex. 6-5 | HR-TAC-A | 70 | — | — | 30 | — | — | — | i | 0.4 | B | 1.430 |
| Ex. 6-6 | HR-TAC-A | 50 | — | — | 50 | — | — | — | 1 | 0.3 | C | 1.420 |
| Ex. 6-7 | HR-TAC-B | 70 | — | — | 30 | — | — | — | 1 | D.6 | B | 1.430 |
| Ex. 6-8 | HR-TAC-B | 50 | — | — | 50 | — | — | — | 1 | 0.5 | C | 1.420 |
| Ex. 6-9 | HR-TAC-A | 34 | — | — | — | — | 30 | 120 | 1 | 0.6 | A | 1.467 |
| Ex. 6-10 | HR-TAC-A | 26 | — | — | — | — | 50 | 80 | 1 | 0.7 | A | 1.475 |
| Ex. 6-11 | HC-PET | — | 90 | — | 10 | — | — | — | — | 1.8 | B | 1.465 |
| Ex. 6-12 | HC-PET | — | 80 | — | — | 20 | — | — | — | 2.0 | A | 1.482 |
| Ex. 6-13 | HC-PET | — | 70 | 30 | — | — | — | — | — | 1.5 | C | 1.441 |
| Ex. 6-14 | HC-PET | — | 60 | 40 | — | — | — | — | — | 1.2 | C | 1.430 |
| Comp. Ex. 5 | HC-PET | — | — | 100 | — | — | — | — | — | 0.4 | D | 1.368 |
| Comp. Ex. 6 | HR-TAC-A | — | — | — | — | 100 | — | — | 1 | 1.0 | A | 1.507 |
| Comp. Ex. 7 | HR-TAC-A | — | — | — | 100 | — | — | — | 1 | 0.3 | D | 1.385 |

What is claimed is:

1. Fluorine-containing tetrafunctional (meth)acrylate represented by the formula (1):

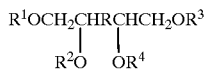

(1)

wherein $R^1$, $R^2$, $R^3$, and $R^4$ are the same or different groups, and each stands for an acryloyl group or a methacryloyl group, and R stands for a fluoroalkylene group having 2 to 12 carbon atoms and 2 or more fluorine atoms.

2. A fluorine-containing monomer composition comprising 5 to 100% by weight of a fluorine-containing tetrafunctional (meth)acrylate represented by the formula (1):

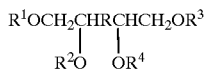  (1)

wherein $R^1$, $R^2$, $R^3$ and $R^4$ are the same or different groups and each stands for an acryloyl or a methacryloyl group, and R stands for a fluoroalkylene group having 2 to 12 carbon atoms and 2 or more fluorine atoms.

3. The monomer composition as claimed in claim 2 further comprising a material selected from the group consisting of a thermosetting monomer, energy-beam curable monomer, monofunctional (meth)acrylate, fluorine containing monomer comprising two (meth)acryloyl groups, fluorine containing monomer comprising three (meth)acryloyl groups, inorganic powders, and mixtures thereof.

4. The monomer composition as claimed in claim 3, wherein said fluorine containing monomer comprising two (meth)acryloyl groups is represented by one of formulas (3), (4), or (5):

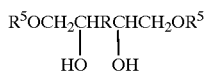  (3)

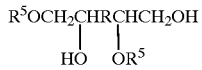  (4)

  (5)

wherein $R^5$ stands for a methacryloyl group and R stands for a fluoroalkylene group having 2 to 12 carbon atoms and 2 or more fluorine atoms.

5. The monomer composition as claimed in claim 4 wherein said monomer composition comprises 10 to 80% by weight of said fluorine containing monomer represented by one of formulas (3), (4), or (5).

6. The monomer composition as claimed in claim 3 wherein said fluorine containing monomer comprising three (meth)acryloyl groups is represented by one of formulas (6) or (7):

  (6)

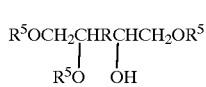  (7)

wherein $R^5$ stands for a methacryloyl group and R stands for a fluoroalkylene group having 2 to 12 carbon atoms and 2 or more fluorine atoms.

7. The monomer composition as claimed in claim 6 wherein said monomer composition comprises 10 to 90% by weight of said fluorine containing monomer represented by one of formulas (6) or (7).

8. A low refractivity material having refractive index of 1.49 or lower prepared by a method comprising the step of curing said monomer composition as claimed in claim 2 by polymerization.

9. A reflection reducing film comprising a transparent substrate and a layer of said low refractivity material as claimed in claim 8.

10. The reflection reducing film as claimed in claim 9 further comprising at least one material layer between the transparent substrate and the layer of the low refractivity material.

11. The reflection reducing film as claimed in claim 10 wherein said material layer is a layer of a refractivity material having refractive index of 1.55 or higher.

12. The reflection reducing film as claimed in claim 9 further comprising a coating for improving abrasion resistance.

* * * * *

UNITED STATES PATENT AND TRADEMARK OFFICE
CERTIFICATE OF CORRECTION

PATENT NO.   : 6,254,973 B1                                                    Page 1 of 1
DATED        : July 3, 2001
INVENTOR(S)  : Tatsurou Yoshida et al.

It is certified that error appears in the above-identified patent and that said Letters Patent is hereby corrected as shown below:

<u>Title page,</u>
Item [75], Inventors, change "Tomoyuki Ikeda; Tetsuya Itoh, both of Tsukuba" to
-- Tomoyuki Ikeda, Tsukuba; Tetsuya Itoh, Nagano --

Signed and Sealed this

Seventeenth Day of December, 2002

JAMES E. ROGAN
*Director of the United States Patent and Trademark Office*